(12) United States Patent
Lo

(10) Patent No.: US 11,690,803 B2
(45) Date of Patent: Jul. 4, 2023

(54) TUMOR PH-SHIFTABLE COATING AND THE NUCLEUS-DIRECTED NANOPARTICLES FACILITATE THE TARGETED CHEMOTHERAPY AND GENE THERAPY AGAINST MULTIPLE CANCERS AND USE THEREOF

(71) Applicant: National Yang Ming Chiao Tung University, Taipei (TW)

(72) Inventor: Yu-Li Lo, Taipei (TW)

(73) Assignee: NATIONAL YANG MING CHIAO TUNG UNIVERSITY, Taipei (TW)

( * ) Notice: Subject to any disclaimer, the term of this patent is extended or adjusted under 35 U.S.C. 154(b) by 10 days.

(21) Appl. No.: 16/858,261

(22) Filed: Apr. 24, 2020

(65) Prior Publication Data

US 2020/0368161 A1    Nov. 26, 2020

Related U.S. Application Data

(60) Provisional application No. 62/839,309, filed on Apr. 26, 2019.

(51) Int. Cl.
| | | |
|---|---|---|
| *A61K 9/127* | (2006.01) | |
| *A61P 35/00* | (2006.01) | |
| *B82Y 5/00* | (2011.01) | |
| *A61K 9/51* | (2006.01) | |
| *A61K 47/62* | (2017.01) | |
| *A61K 31/7105* | (2006.01) | |
| *A61K 45/06* | (2006.01) | |

(52) U.S. Cl.
CPC ............ *A61K 9/127* (2013.01); *A61K 9/5123* (2013.01); *A61K 9/5153* (2013.01); *A61K 31/7105* (2013.01); *A61K 47/62* (2017.08); *A61P 35/00* (2018.01); *A61K 45/06* (2013.01); *B82Y 5/00* (2013.01)

(58) Field of Classification Search
None
See application file for complete search history.

(56) References Cited

U.S. PATENT DOCUMENTS

2017/0151339 A1* 6/2017 White .................. A61K 9/5169
2020/0375912 A1* 12/2020 Serda ..................... A61K 9/127

* cited by examiner

*Primary Examiner* — Celeste A Roney
(74) *Attorney, Agent, or Firm* — Muncy, Geissler, Olds & Lowe, P.C.

(57) ABSTRACT

At present, there is a great need for the development of new tumor pH-shiftable nanoparticles that are effective to reduce side effects, enhance active tumor focusing, improve the cellular uptake, and nuclear/cytoplasmic targeting of chemotherapy and gene therapeutic. Hence, we designed novel solid lipid nanoparticles (SLN) and liposomes (Lip) to deliver microRNA and antineoplastic agent, respectively. The designed SLN and liposomes incorporating microRNA and anticancer drugs in the core, which is surrounded by lipids modified with peptide T (a ligand plus a cell-penetrating peptide) and a nucleus-targeted sequence of peptide R as the inner shell. Moreover, coating a pH-responsive polymer (PGA-PEG) on the outer layer of Lip-TR (PGA-Lip-TR) and SLN-T (PGA-SLN-T) can protect the peptide T and R from degradation by peptidases during systemic circulation and enhance directing to the acidic tumor sites. Collectively, these pH-shiftable nanoparticles may provide a novel and potential strategy for anticancer therapy.

23 Claims, 53 Drawing Sheets
Specification includes a Sequence Listing.

DSPE-PEG

T peptide

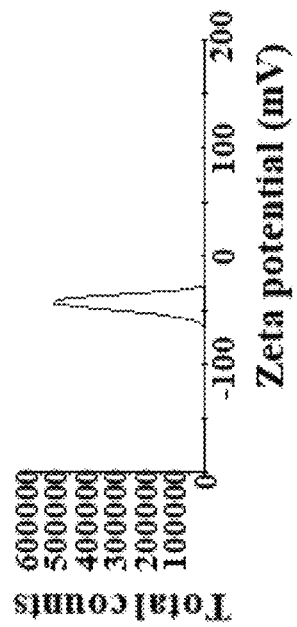
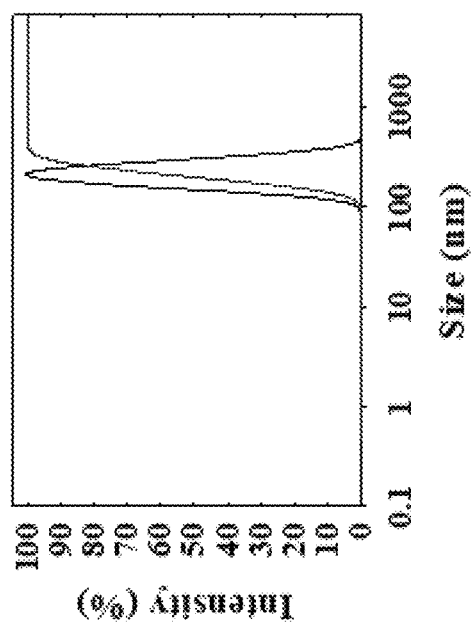
Fig 2D
Fig 2C

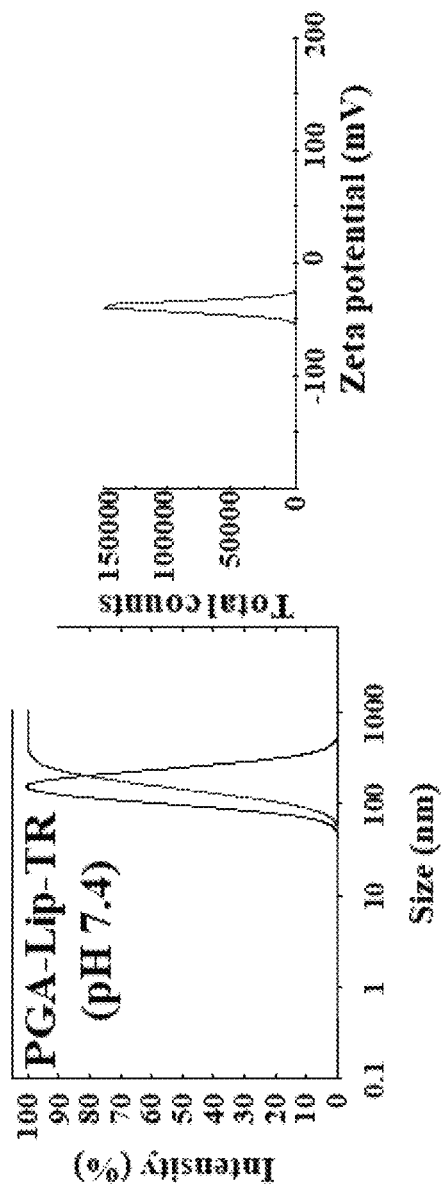

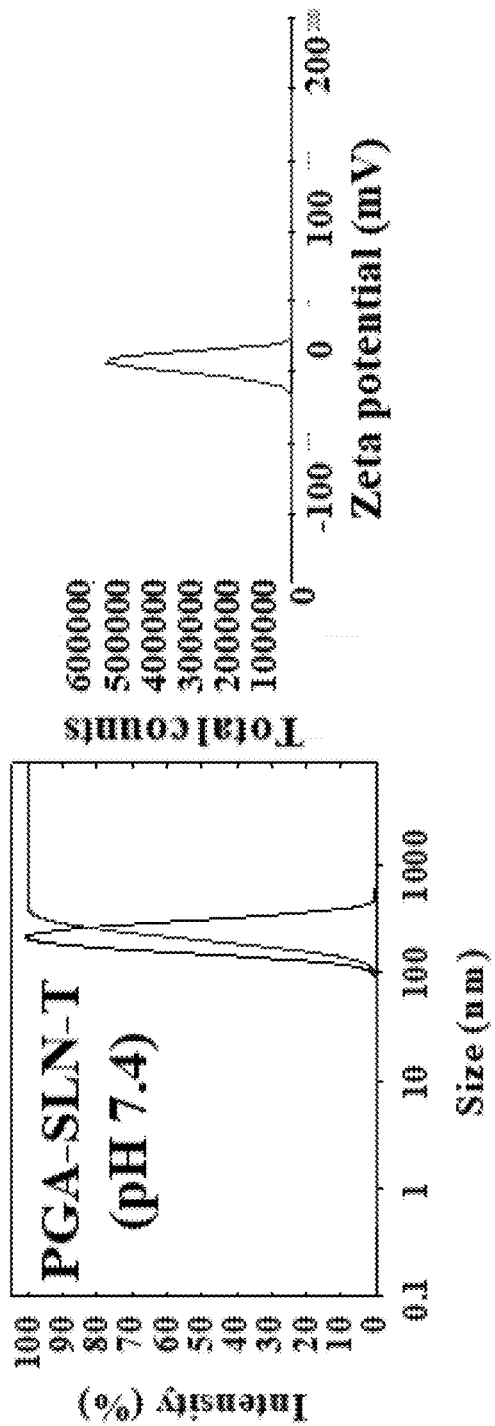

TUMOR PH-SHIFTABLE COATING AND THE NUCLEUS-DIRECTED NANOPARTICLES FACILITATE THE TARGETED CHEMOTHERAPY AND GENE THERAPY AGAINST MULTIPLE CANCERS AND USE THEREOF

CROSS-REFERENCE TO RELATED APPLICATIONS

This non-provisional application claims priority under 35 U.S.C. § 119(a) on Patent Application No. 62/839,309 filed in American United States Apr. 26, 2019, the entire contents of which are hereby incorporated by reference.

FIELD OF THE INVENTION

The present invention relates to novel tumor pH-shiftable nanoparticles and use thereof.

BACKGROUND OF THE INVENTION

Cancer is one of the leading public health problem worldwide. Platinum-related compounds, including oxaliplatin, are commonly-used chemotherapeutic agents for the treatment of 70% of solid tumors, such as colorectal, gastric, pancreatic, esophageal, non-small and small cell lung, breast, testicular, cervical, and ovarian cancers. Among various treatment regimen, oxaliplatin (Oxa), a third-generation platinum derivative, is approved in combination with 5-fluorouracil (5-FU) and leucovorin (FOLFOX) as the first-line therapy for CRC of metastatic or advanced stage. Such treatment is effective initially. However, non-selective chemotherapeutic drugs usually led to serious side effects. However, intact oxaliplatin and the metabolite of oxaliplatin, oxalate, have been reported to be pumped out by P-glycoprotein (P-gp) and multidrug-resistance associated proteins (MRP), which are all involved in the occurrence of multidrug resistance (MDR) in cancer therapy. Moreover, another burden for oxaliplatin therapy arises from its side effects such as nausea, diarrhea, low blood cell counts and neurotoxicity. In addition, oxaliplatin displays high volume of distribution, due to its irreversible plasma or tissue protein binding and rapid distribution into erythrocytes, which hamper its arrival at the target tumor sites.

Over the past decade, accumulating evidences have demonstrated that microRNA (miRNA; miR) therapy is effective against several malignancies. Among various miR, the expression of miR-320 was downregulated in colorectal cancer, cervical cancer, and oral cancer. Besides, miR-320 played a tumor-suppressive role in regulating tumor epithelial-mesenchymal transition (EMT), apoptosis, migration, invasion, proliferation, and drug resistance in different cancers such as colorectal cancer, cervical cancer, oral cancer and gastric cancer.

However, miR is unstable in biological systems due to rapid degradation and fast elimination by kidney filtration. MiR may also have the disadvantages of triggering innate immune system and possible off-target effects. Additionally, the major challenge in oxaliplatin treatment is its high drug toxicity and side effects caused by unselective uptake by normal cells.

Nanoscale drug delivery systems, such as liposomes (Lip) and solid lipid nanoparticles (SLN) are emerging and potential strategies for delivering miRNAs and chemotherapeutic drugs for cancer therapy, since they improve pharmacokinetic properties, sustain or control drug release and reduce cargo toxicity. Although polyethylene glycol (PEG)-modified drugs or nanocarriers are currently available on the market with the advantage of increasing the systemic circulation time of nanocarriers, their uptake into cancer cells is limited, thus reducing the therapeutic effect.

At present, there is a great need for the development of new tumor pH-shiftable nanoparticles that are effective to reduce side effects, enhance active tumor focusing, prevent tumor targeting peptide cleavage by peptidases and improve the cellular uptake and/or nucleus targeting of chemotherapy. Hence, we developed novel SLN-T and Lip-TR to deliver miR-320 and oxaliplatin, respectively. The designed SLN and Lip incorporating miR and anticancer drugs in the core, which is surrounded by lipids modified with peptide T (a ligand plus a cell-penetrating peptide) and a nucleus-targeted sequence of peptide R as the inner shell, as well as a pH-sensitive polymer PEG-PGA as the outer shell to protect the peptide T and R from degradation by peptidases.

SUMMARY OF THE INVENTION

In view of the above-mentioned problem, the present invention provides a novel tumor pH-shiftable nanoparticles and use thereof.

The invention present a pH-shiftable nanoparticles, comprising: a surface and a nanoparticle core, wherein the surface of the nanoparticle core is modified with a cationic target molecule; a therapeutic agent inside the nanoparticle core; and an outer layer, surrounding outside of the nanoparticle core, the outer layer is coating with an acid-detachable polymer, the acid-detachable polymer have the characteristic of responding to acidic pH; wherein the cationic target molecule of the nanoparticle core and the acid-detachable polymer of the outer layer, which form a space and charge barrier via the electrostatic interaction In one embodiment, the acid-detachable polymer is PGA-PEG.

The tumor pH-shiftable nanoparticles, wherein the nanoparticle core is L-α-phosphatidylcholine (PC), glycerol monostearate (monostearin), glycerol monopalmitate, glycerol monooleate, DSPE, DPPE, DOPE, DOTAP, DOTMA, SAINT 2, MC3 or KC2.

The pH-shiftable nanoparticles, wherein the therapeutic agent is a microRNA or a drug.

The pH-shiftable nanoparticles, wherein the therapeutic agent is a microRNA, and the microRNA is a hsa-miR-21 inhibitor or a microRNA mimic, wherein the microRNA mimic is selected from the group consisting of has-miR-122-5p, hsa-miR-125b-5p, has-miR-136-5p, has-miR-139-5p, hsa-miR-142-5p, has-miR-200c-3p and has-miR-320a.

The pH-shiftable nanoparticles, wherein the therapeutic agent is a drug, and the drug is selected from the group consisting of irinotecan, oxaliplatin, epirubicin, doxorubicin, afatinib and docetaxel.

The pH-shiftable nanoparticles can be accumulated in the cancer cell in pH 5-7 environment or tumor microenvironment and the outer layer responding to tumor acidic pH to become protonated and detached from the inner layer of the nanoparticle core.

In one embodiment, the nanoparticle core is a solid lipid nanoparticles (SLN) or a liposomes (LIP).

The pH-shiftable nanoparticle's cationic target molecule is a peptide.

The pH-shiftable nanoparticle's peptide is a cell-penetrating peptide, and the cell-penetrating peptide is TAT peptide (SEQ. NO 1)

The pH-shiftable nanoparticle's peptide is a tumor-homing peptide, and the tumor-homing peptide is N peptide (SEQ. NO 2)

The pH-shiftable nanoparticle's peptide is a bifunctional peptide which conjugate the cell-penetrating peptide and the tumor target peptide (ligand), and the bifunctional peptide is T peptide (SEQ. NO 3).

In one embodiment, the bifunctional molecule of the pH-shiftable nanoparticle is constructed by the conjugate (DSPE-PEG-T) of lipid and the bifunctional peptide.

The pH-shiftable nanoparticle's peptide is a cell nucleus-targeted peptide is R peptide (SEQ. NO 4).

In one embodiment, wherein the nanoparticle is constructed by the conjugate (DSPE-PEG-R) of lipid and cell nucleus-targeted peptide.

A pharmaceutical composition comprising: as mentioned above of an effective amount of pH-shiftable nanoparticles.

The pharmaceutical composition of the pH-shiftable nanoparticles comprising: a microRNA-loaded pH-shiftable nanoparticle, wherein the lipid is a mixture of a monoglyceride, a cationic lipid and a surfactant, and the therapeutic agent is a microRNA; and a drug-loaded pH-shiftable nanoparticle, wherein the lipid is a lipid bilayer composed of a phospholipid and the therapeutic agent is an anticancer drug.

In one embodiment, the microRNA of the pharmaceutical composition is a hsa-miR-21 inhibitor or a microRNA mimic, wherein the microRNA mimic is selected from the group consisting of has-miR-122-5p, hsa-miR-125b-5p, has-miR-136-5p, has-miR-139-5p, hsa-miR-142-5p, has-miR-200c-3p and has-miR-320.

In one embodiment, the microRNA-loaded pH-shiftable nanoparticle, wherein the microRNA-loaded pH-shiftable nanoparticle is SLN and the microRNA is miR-320.

In one embodiment, the anticancer drug of the pharmaceutical composition is selected from the group of irinotecan, oxaliplatin, epirubicin, doxorubicin, afatinib and docetaxel.

In one embodiment, the drug-loaded pH-shiftable nanoparticle is Lip and the anticancer drug is Oxa.

In one embodiment, the drug-loaded pH-shiftable nanoparticle, the pH-shiftable nanoparticle is modified with peptide T and peptide R (Lip-TR).

In one embodiment, the microRNA-loaded pH-shiftable nanoparticle is modified with peptide T (SLN-T).

In one embodiment, the coating of pH-sensitive polymer (PGA-PEG) on the outer layer can protect the peptides such as peptide T and R from degradation by peptidases during systemic circulation and enhance directing to the acidic tumor sites.

In one embodiment, the coating of pH-sensitive polymer on the outer layer can increase the cellular uptake at pH 6.0.

A method for treating cancer in a subject, comprising: administering an effective amount of pH-shiftable nanoparticle as mentioned above, comprising: a microRNA-loaded pH-shiftable nanoparticle, wherein the lipid is a mixture of a monoglyceride, a cationic lipid, and a surfactant and the therapeutic agent is a microRNA; and a drug-loaded pH-shiftable nanoparticle, wherein the lipid is a lipid bilayer composed of a phospholipid and the therapeutic agent is an anticancer drug.

In one embodiment, wherein the cancer is colorectal cancer, head and neck cancer, gastric cancer or cervical cancer.

In one embodiment, wherein the anticancer drug is selected from the group consisting of irinotecan, oxaliplatin, epirubicin, doxorubicin, afatinib and docetaxel.

In one embodiment, wherein the microRNA is a hsa-miR-21 inhibitor or a microRNA mimic, wherein the microRNA mimic is selected from the group consisting of has-miR-122-5p, hsa-miR-125b-5p, has-miR-136-5p, has-miR-139-5p, has-miR-200c-3p, and has-miR-320.

BRIEF DESCRIPTION OF THE DRAWINGS

FIG. 2C-2D shows the size and zeta potential of PGA-SLN-T. The PGA-SLN-T was negatively charged with small PDI value, N=3.

FIG. 3A-3D shows the pH-responsive changes in size, zeta potential of PGA-Lip-TR/Oxa at pH 7.4 and pH 6.0. The changes in size and zeta potential of PGA-Lip-TR/Oxa was measured by Zetasizer after incubating with pH 7.4 or pH 6.0 PBS for 15 min. PGA coating increased the pH-responsive changes in particle size and zeta potential of PGA-Lip-TR/Oxa at pH 6.0. The particle size was reduced and zeta potential of PGA-Lip-TR was increased with decreasing pH value, demonstrating that the pH-sensitive PGA coating could be detached from nanoparticles under acidic environment.

FIG. 3E-3H shows the changes in size and zeta potential of PGA-SLN-T/miR-320 was measured by Zetasizer after incubating with pH 7.4 or pH 6.0 PBS for 15 min. PGA coating increased the pH-shiftable changes in particle size and zeta potential of PGA-SLN-T/miR-320 at pH 6.0. The particle size and zeta potential of PGA-SLN-T was increased with decreasing pH value, demonstrating that the pH-sensitive coating could be detached from nanoparticles under acidic environment.

FIGS. 6A-6C show the different treatments of SLN/miR-320 and/or Lip-TR/Oxa inhibited migration and downregulated EMT-associated protein expressions in cancer cells, indicating that these formulations inhibited tumor metastasis and invasion.

DETAILED DESCRIPTION OF THE INVENTION

Figure 1A:
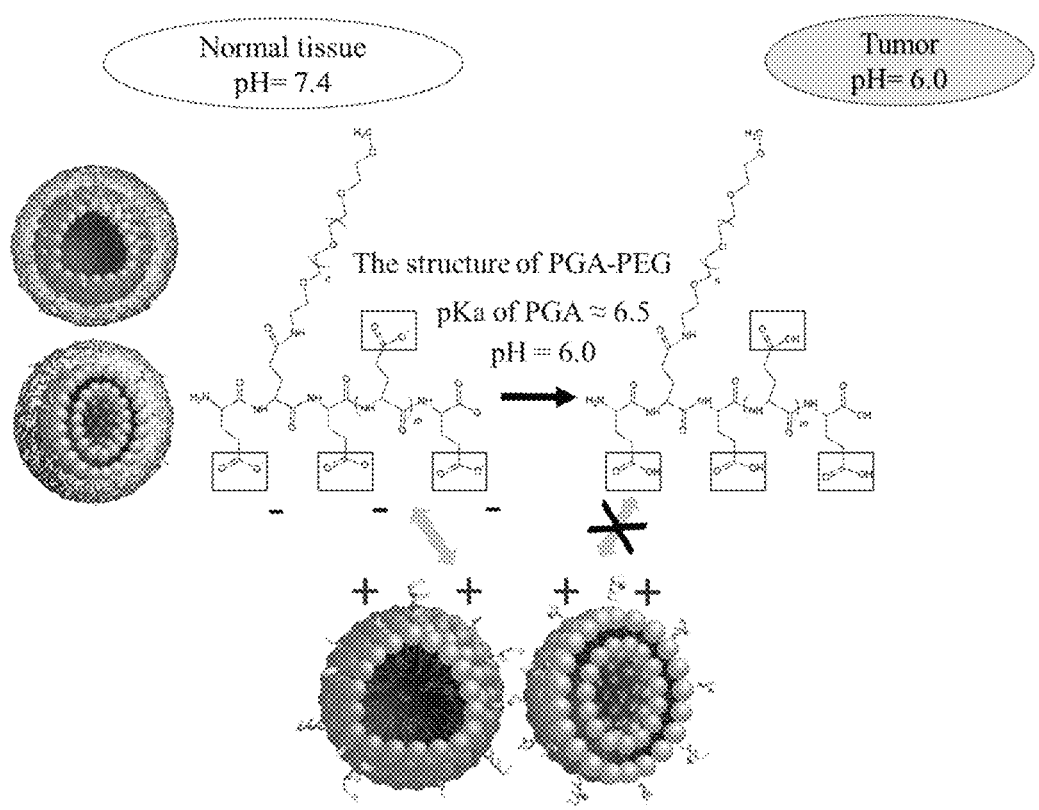
FIG. 1A shows the schematic illustration of the pH-sensitive PGA-coating responding to tumor acidic pH to become protonated and detached from inner layer of SLN-T/miR-320 and Lip-TR/Oxa.
Figure 1B:
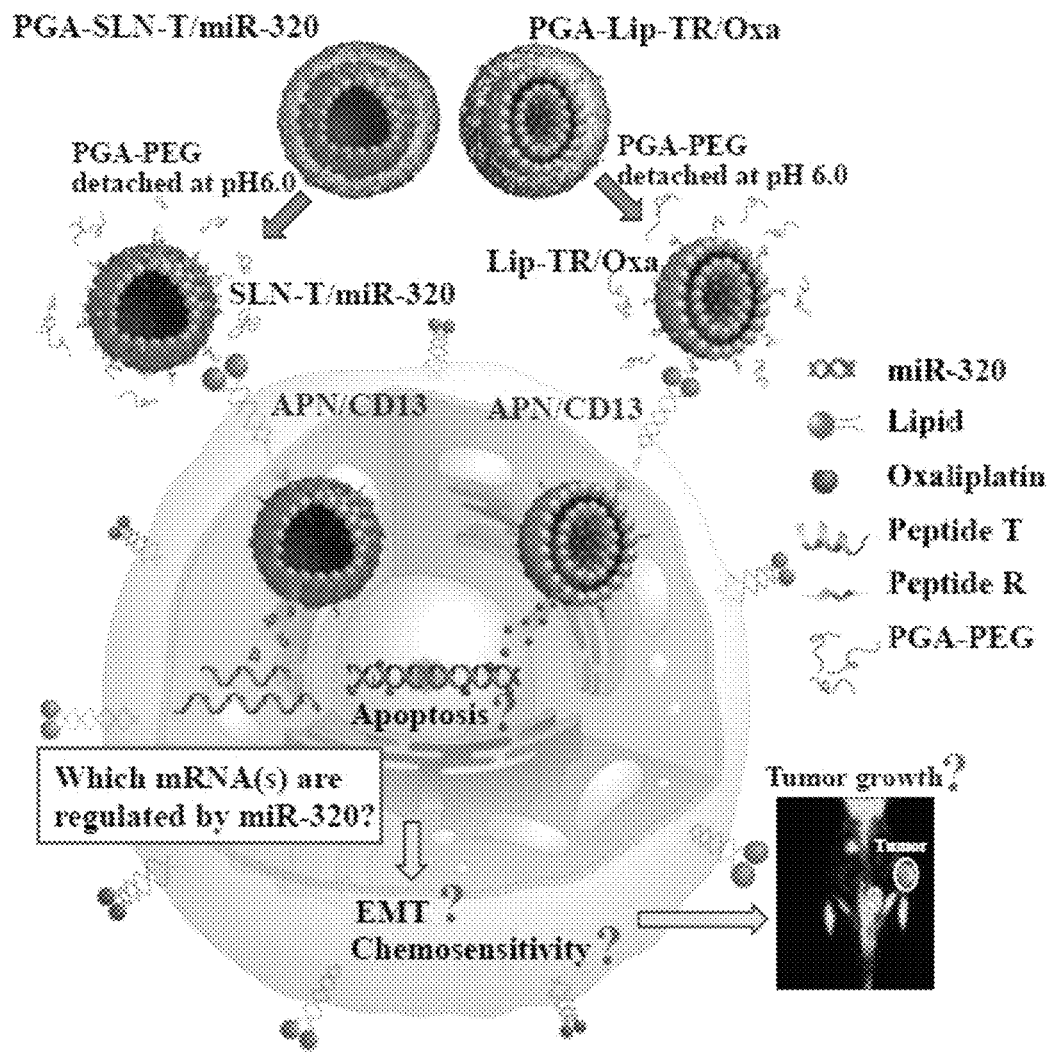
FIG. 1B shows the schematic design of the pH-shiftable PGA-SLN-T/miR-320 and PGA-Lip-TR/Oxa, which are sensitive to tumor extracellular pH to approach tumor-specific nuclear and cytoplasmic targets and increased cytotoxicity against cancer cells.

In order to solve the above-mentioned problems, the present invention provides a novel tumor pH-shiftable nanoparticles and use thereof.

T peptide AYGRKKRRQRRRCRNGRGPDC (SEQ. NO 3) is a conjugated peptide of TAT CAYGRKKRRQRRR (SEQ. NO 1) and NGR (N) RNGRGPDC (SEQ. NO 2) with the function of high cellular penetration and tumor targeting ability. The trans-acting activator of transcription protein (TAT), which was derived from human immunodeficiency virus type-1 (HIV-1) and is one of the most studied cell-penetrating peptides (CPP). T peptide (SEQ. NO 3) possesses features of tumor-homing moiety and cell-penetrating property, thus avoiding unspecific drug uptake into the normal cells.

R peptide CRRKRRRRR (SEQ. NO 4) is a human-originated nuclear localization sequence (NLS) from human phosphatidate phosphatase (LPIN3). R peptide is thus used to act as both a CPP and a nucleus-targeted peptide for the direct localization of anticancer drugs into the cell nucleus. Nevertheless, peptides may be cleaved by peptidases during the systemic circulation.

Oxaliplatin is a third-generation platinum derivative and is currently the first line treatment of advanced colorectal cancer (CRC) in combination with 5-fluorouracill (5-FU) and leucovorin as FOLFOX. Such treatment is effective initially.

However, intact oxaliplatin and the metabolite of oxaliplatin, oxalate, have been reported to be pumped out by P-glycoprotein (P-gp) and multidrug-resistance associated proteins (MRP), which are all involved in the occurrence of multidrug resistance (MDR) in cancer therapy. Moreover, another burden for oxaliplatin therapy arises from its side effects such as nausea, diarrhea, low blood cell counts and neurotoxicity. In addition, oxaliplatin displays high volume of distribution, due to its irreversible plasma or tissue protein binding and rapid distribution into erythrocytes, which hamper its arrival at the target tumor sites.

The microRNA (miRNA; miR) therapy is effective against several malignancies. Among various miR, the expression of miR-320 was downregulated in colorectal cancer, cervical cancer and oral cancer. Besides, miR-320 played a tumor-suppressive role in regulating tumor epithelial-mesenchymal transition (EMT), apoptosis, migration, invasion, proliferation, and drug resistance in different cancers such as colorectal cancer, cervical cancer, oral cancer and gastric cancer.

However, miR is unstable in biological systems due to rapid degradation by endo- and exonucleases and fast elimination by kidney filtration. Furthermore, it has difficulty to penetrate the cell membrane because of its negative charge. MiR may also have the disadvantages of triggering innate immune system and possible off-target effects. Moreover, miR usually possesses 20-24 nucleotides with low molecule weight and low charge density.

Platinum-related compounds, including oxaliplatin, are commonly-used chemotherapeutic agents for the treatment of 70% of solid tumors, such as colorectal, gastric, pancreatic, esophageal, non-small and small cell lung, breast, testicular, cervical, and ovarian cancers.

Oxaliplatin (Oxa) is approved in combination with 5-fluorouracil (5-FU) and leucovorin (FOLFOX) as the first-line therapy for CRC of metastatic or advanced stage. However, non-selective chemotherapeutic drugs usually led to serious side effects.

Here, we designed novel peptide-modified liposomes, Lip-TR, which is capable of increasing cellular uptake, nuclear localization and targeting to specific receptors, and is well suitable for delivering Oxa. In addition, miR-320 has been proved to induce apoptosis, inhibit proliferation and epithelial-mesenchymal transition of cancer cells. Cationic solid lipid nanoparticles (SLN) may serve as a promising carrier for miRNA delivery. Moreover, coating pH-shiftable polymer (PGA-PEG) on the outer layer of Lip-TR (PGA-Lip-TR) and SLN (PGA-SLN) can prolong the circulation time of nanoparticles in blood and enhance specific targeting to the acidic tumor sites.

The term "miR-c" as used herein refers to miR-320.

Example 1. Synthesis of PGA-PEG

Figure 1C:
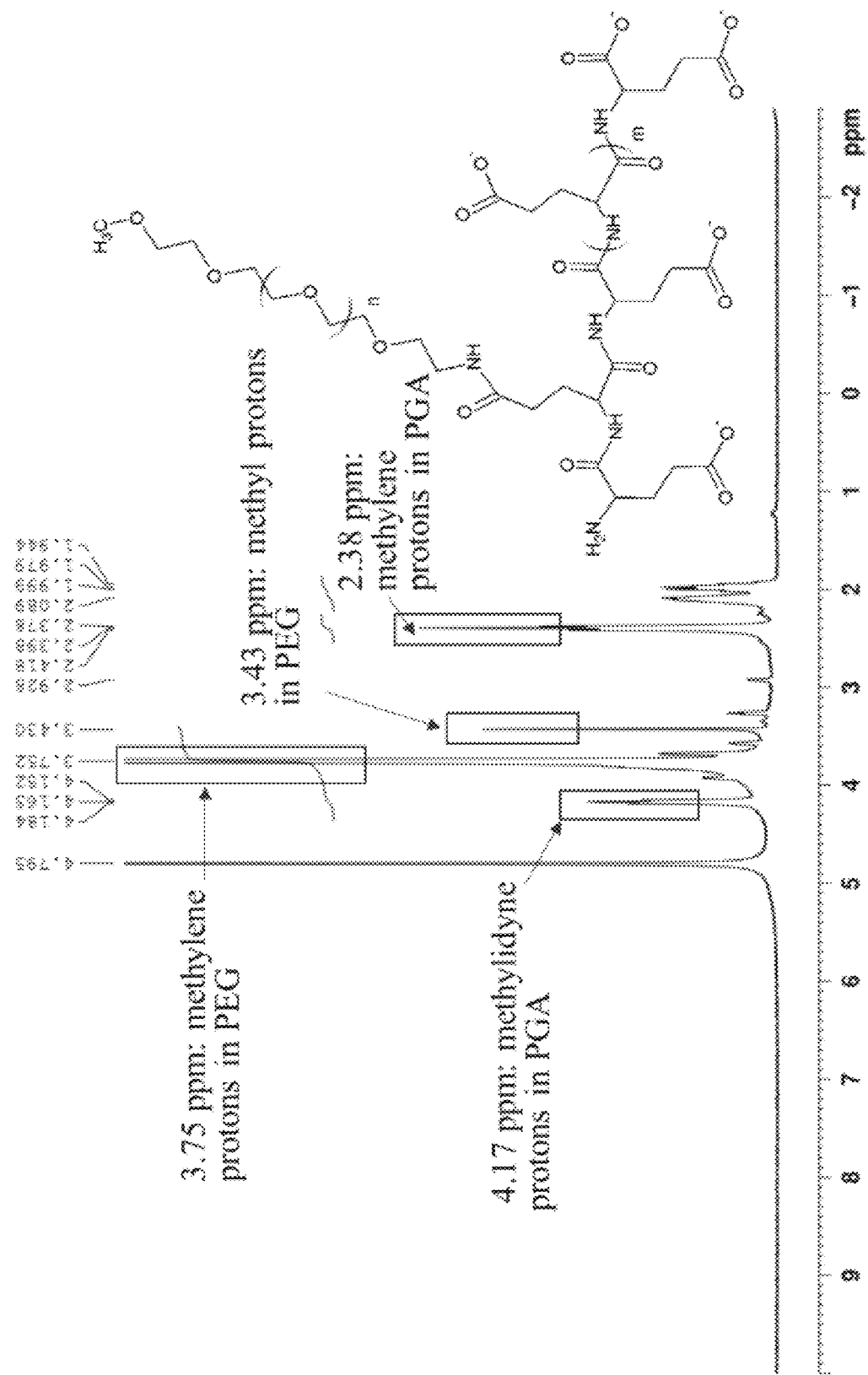
FIG. 1C shows the $^1$H NMR spectrum of PGA-PEG. The PGA-PEG was successfully synthesized utilizing EDC-NHS chemistry and the structure was verified by H NMR.
Figure 1D:
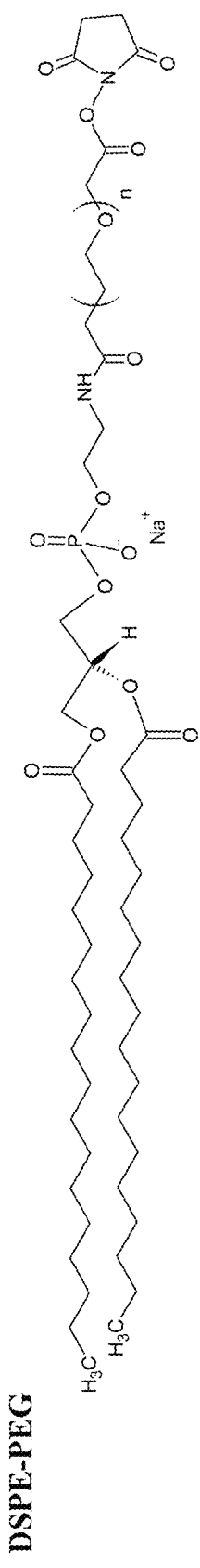
FIG. 1D shows chemical formula of DSPE-PEG.
Figure 1E:
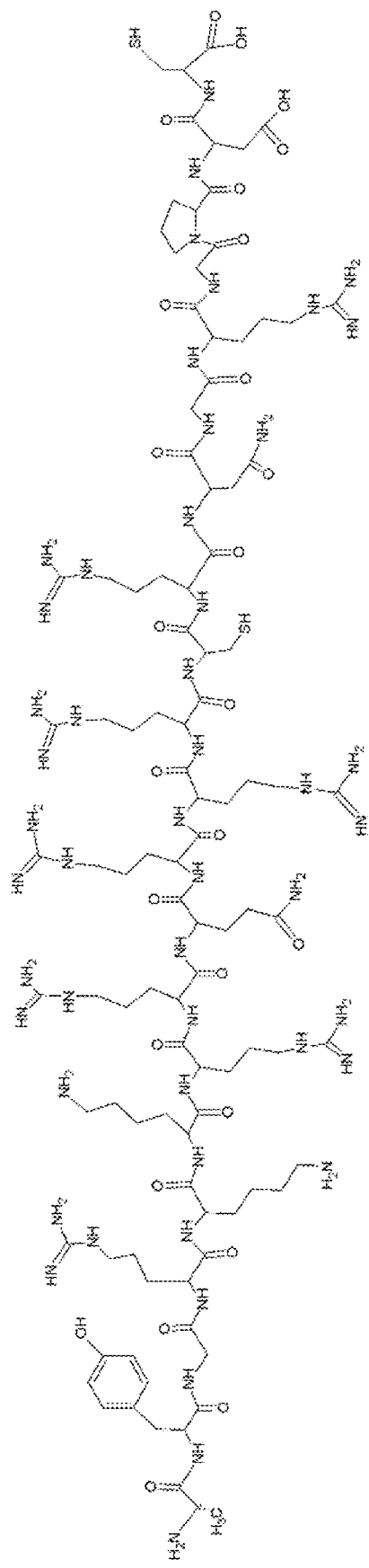
FIG. 1E shows chemical formula of T Peptide.

PGA, mPEG-NH2, and NHS were dissolved in 1 ml sodium tetraborate. EDC was added in the mixture with stirring. The reaction was carried out overnight at room temperature. Then, the reaction mixture was dialyzed with a 5 kDa cut-off membrane against PBS for 24 h. The powder of PGA-PEG was obtained by lyophilization and the structure was measured by $^1$H NMR (FIG. 1C). The $^1$H NMR of PGA-PEG (D20, 400 MHz): δ=2.25 (—CH-CH2-CO—); 3.35 (—CH3); 3.67 (—CH2-CH2-O— of the PEG block); 4.29 (—NH—CH— CO— in glutamic acid).

Example 2. Synthesis of DSPE-PEG-Peptides

Figure 1F:
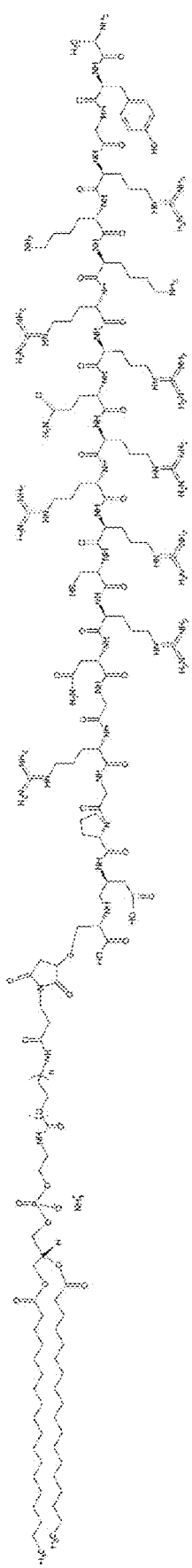
FIG. 1F shows chemical formula of DSPE-PEG-T.
Figure 1G:
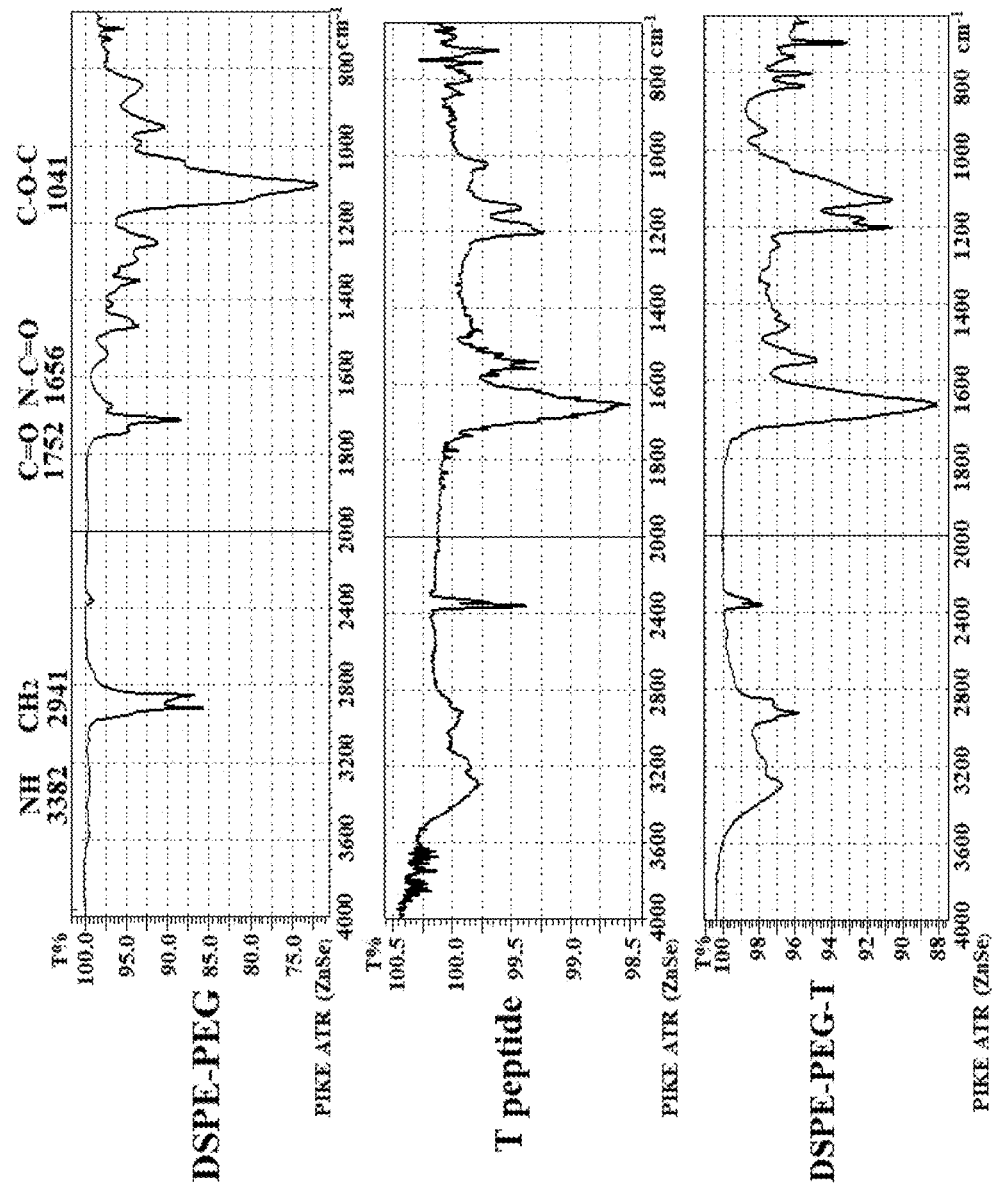
FIG. 1G shows the FT-IR spectrum of DSPE-PEG-T. The DSPE-PEG-T was successfully synthesized and the structure was verified by FT-IR spectrum.
Figure 1H:
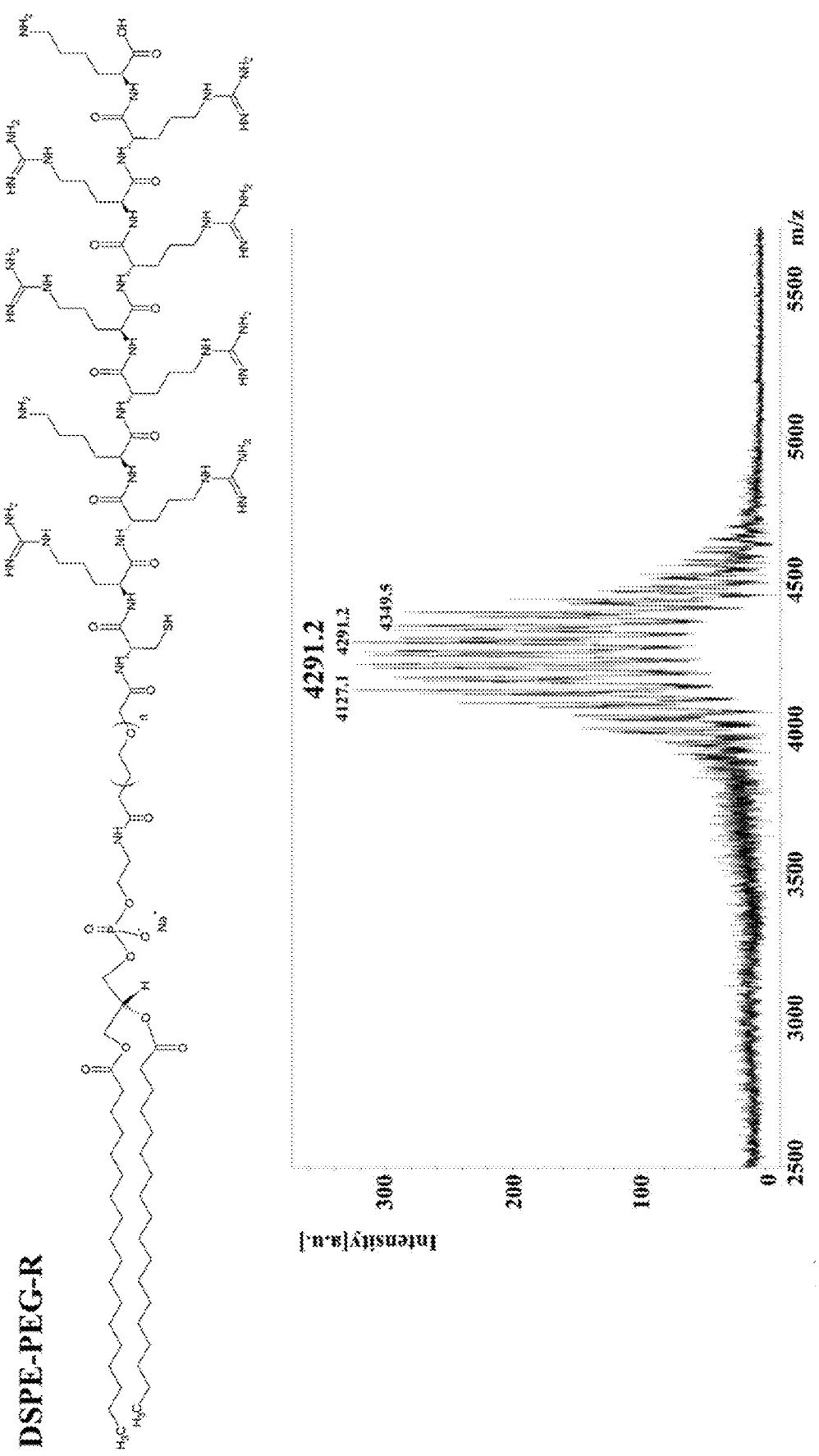
FIG. 1H shows the MALDI-TOF mass spectrum of DSPE-PEG-R. The DSPE-PEG-R was successfully synthesized and the structure was verified by MALDI-TOF mass spectrum.

DSPE-PEG-NHS and peptides with the molar ratio of 1:1.1 were dissolved in water, trimethylamine (TEA) was added to catalyze the reaction. After 24 h reaction, the mixture solvent was dialysis against water with a 2 kDa cut-off membrane to remove the unconjugated reactants. The powder of DSPE-PEG-peptide was obtained by lyophilization and the structure was confirmed by $^1$H NMR (FIG. 1C) and ATR-FTIR FIGS. 1F, 1G.

Example 3. Preparation of Peptide-Conjugated Lip-TR/Oxa and pH-Sensitive PGA-Lip-TR/Oxa Peptide-conjugated and oxaliplatin-loaded liposomes (Lip-TR/Oxa) were prepared via thin film hydration. Briefly, DOTAP, DOPE, DSPE-PEG-T and DSPE-PEG-R were dissolved in chloroform in a round-bottomed flask. The resulting lipid solution was then evaporated at 40° C. using the rotary evaporator to form the lipid film. The solvent was totally evaporated under vacuum. Dried lipid film was hydrated by ammonium sulfate. The liposomes were then extruded through 200 nm and 100 nm membrane filter for three times, respectively. After dialysis with PBS, oxaliplatin was then loaded into liposomes. For preparing pH-sensitive liposomes (PGA-Lip-TR/Oxa), PGA-PEG was added drop by drop into liposomes and then mixed for 4 h at 37° C.

Example 4. Preparation of miRNA-Loaded SLN/miR-320a and pH Sensitive PGA-SLN/miR-320a Monostearin, DOTAP and cholesterol were dissolved in ethanol and heated at 50° C. for 30 min, then poloxamer was added and stirred for 1 h, miR-320a were added drop by drop and mixed by pipetting. For preparing pH-sensitive SLN-T (PGA-SLN/miR-320), 0.1% PGA was added drop by drop into SLN-T/miR-320.

Example 5. Characteristics of PGA-SLN/miR-320 and PGA-Lip-TR/Oxa

Figures 2A, 2B:
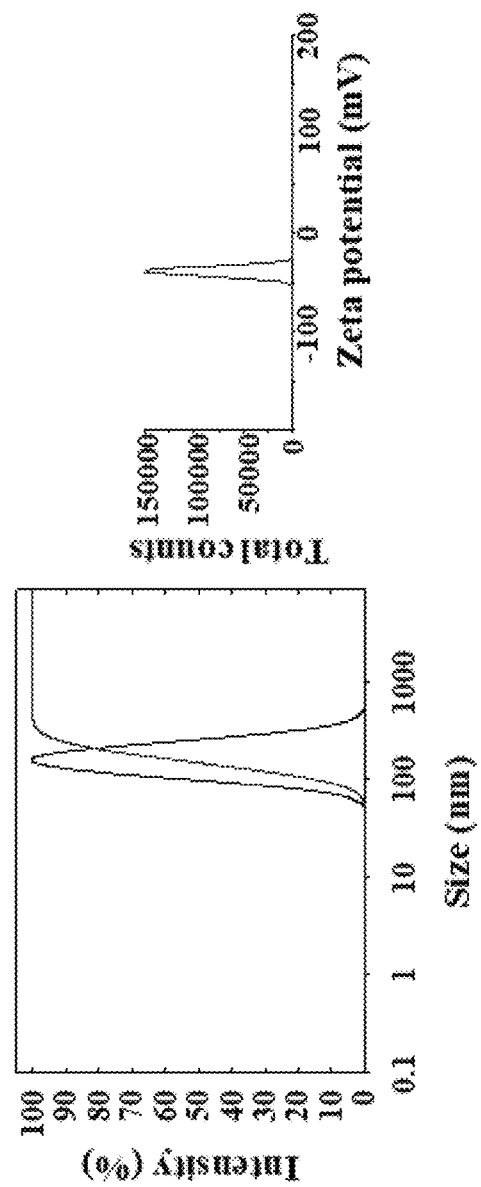
FIG. 2A-2B shows the size and zeta potential of PGA-Lip-TR. The PGA-Lip-TR was negatively charged with small PDI value, N=3.
Figure 2E:
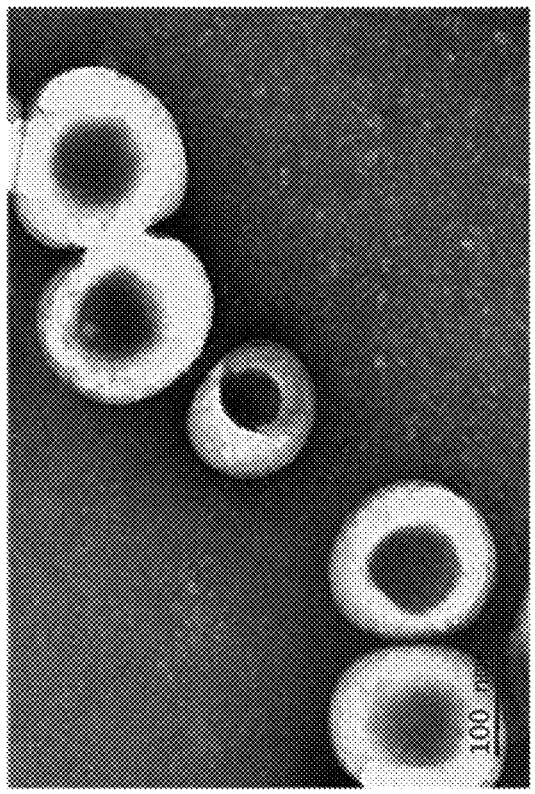
FIG. 2E shows the TEM image of PGA-Lip-TR. The PGA-Lip-TR/Oxa displayed homogeneous nano-size and spherical core-shell shape, N=3.
Figure 2F:
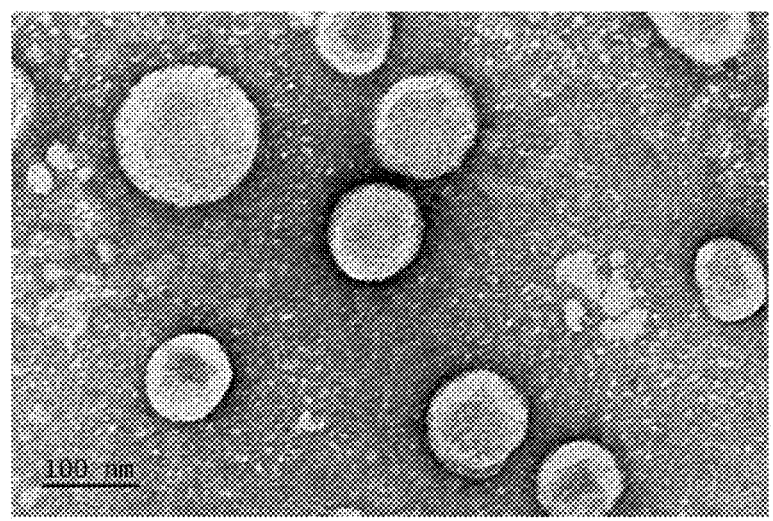
FIG. 2F shows the TEM image of PGA-SLN-T. The PGA-SLN-T/miR-c displayed homogeneous nano-size and spherical core-shell shape. Bar=100 nm. N=3.
Figure 2G:
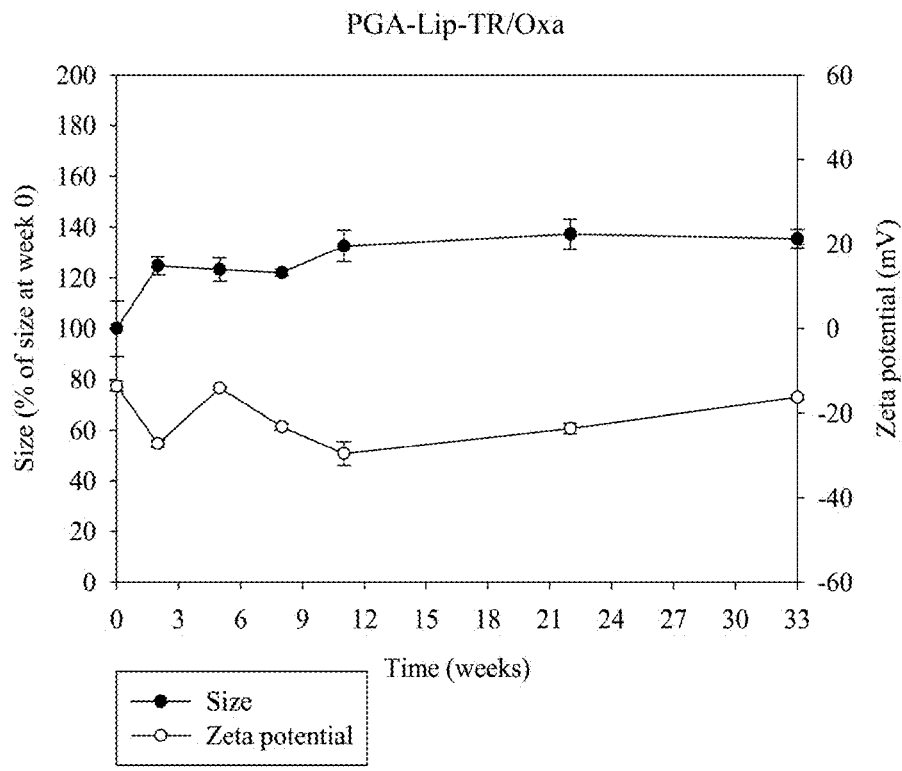
FIG. 2G-2H shows the changes in particle size, zeta potential of PGA-Lip-TR/Oxa measured and PGA-SLN-T/miR-320 for 33 week-storage at 4° C. Stability test: PGA-Lip-TR/Oxa and PGA-SLN-T/miR-320 were stable for 33 weeks.
Figure 2H:
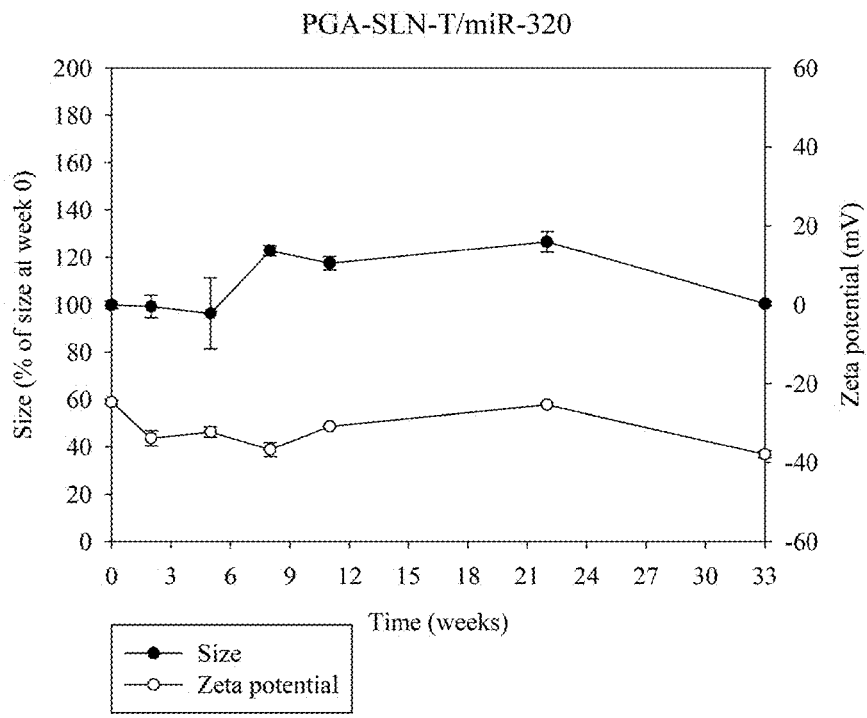
Figure 2I:
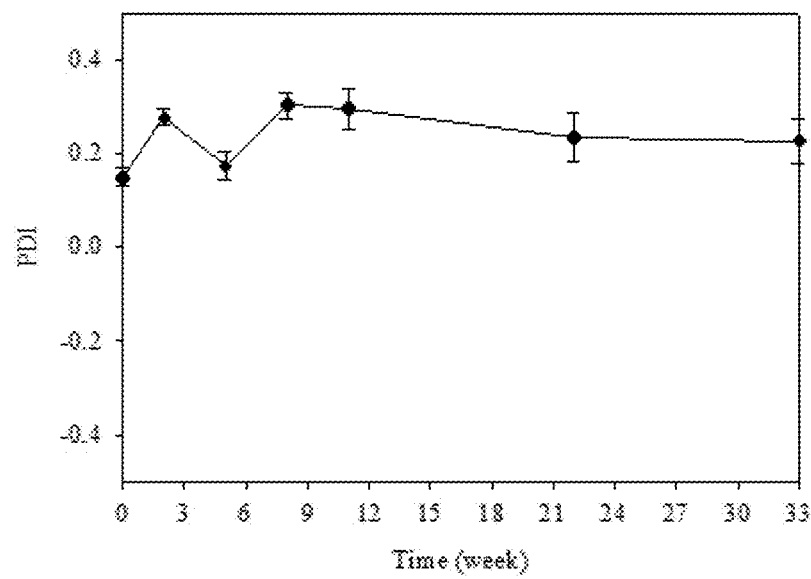
FIG. 2I-2J shows the changes in PDI (polydispersity index) of PGA-Lip-TR/Oxa and PGA-SLN-T/miR-320 measured for 33 week-storage at 4° C. Stability test: PGA-Lip-TR/Oxa and PGA-SLN-T/miR-320 were stable for 33 weeks.
Figure 2J:
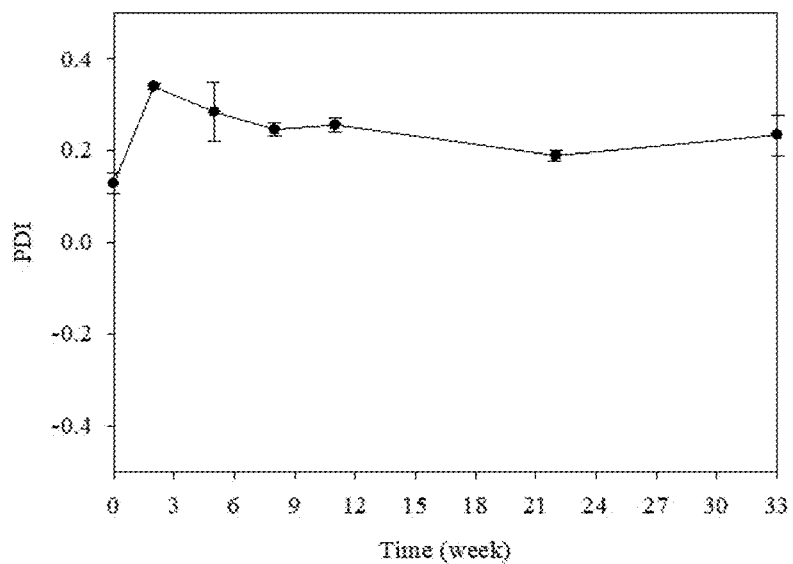

The size distribution (FIG. 2A, 2C) zeta potential (FIG. 2B, 2D) and polydispersity index (PDI) (FIG. 2I, 2J) of PGA-SLN/miR-320 and PGA-Lip-TR/Oxa were measured using a Zetasizer Nano-ZS particle size analyzer (Malvern Instruments Ltd, Malvern, Worcestershire UK). The morphology of these two nanoparticles were observed under a transmission electron microscope (JEM-2000EX II, Japan) with 1% uranyl acetate staining.

Example 6. Encapsulation Efficiency (EE %)

1 mL Lip-TR/Oxa was centrifuged through ultracentrifuge filter. Then, encapsulated oxaliplatin was extracted from the liposomes by triton X-100 and methanol. The extracted oxaliplatin and oxaliplatin in the filtrate were analyzed by HPLC-PDA detector. The HPLC system consists of a pump (S 1130), auto sampler (S 5300) and PDA Detector (S 3345) (Sykam, Eresing, Germany). The solution was degassed by a bath sonicator. The flow rate was 1.0 mL/min at room temperature and detection wavelength at 197 nm. Each experiment was performed in triplicate. EE % was then calculated by the following equation.

$$EE\% = [(C_A - C_F/C_A] \times 1000$$

$C_A$: the concentration of added oxaliplatin
$C_F$ the concentration of oxaliplatin in the filtrate.

Example 7. pH-Induced Size and Zeta Potential Change

The size and zeta potential of PGA-Lip-TR/Oxa (FIG. 3A-3D) and PGA-SLN/miR-320 (FIG. 3E-3H) were measured by Dynamic Light Scattering (DLS) analyzer (Malvern ZetasizerNano ZS90, Worcestershire, UK). After incubating PGA-Lip-TR/Oxa or PGA-SLN/FAM-miR-320 with 1 mL PBS buffer (pH 7.4 and pH 6.0) at RT for 30 min, sample size and zeta potential were measured in triplicate. PGA coating increased the pH-responsive changes in particle size and zeta potential of PGA-Lip-TR/Oxa and PGA-SLN-T/miR-320 at pH 6.0 (Table 1 and FIG. 3I-3J). The particle size and zeta potential of both PGA-Lip-TR and PGA-SLN-T were reduced with decreasing pH value, demonstrating that the pH-sensitive coating could be detached from nanoparticles under acidic environment.

TABLE 1 pH-responsive changes of PGA-Lip-TR and PGA-SLN-T formulations (n = 3; values are mean ± SD).

| Formulations | pH | Size (nm) | PDI$^a$ | Zeta potential (mV) |
|---|---|---|---|---|
| Lip-TR | 7.4 | 101.43 ± 2.55 | 0.16 ± 0.21 | 26.61 ± 1.40 |
| pH = 7.4 PGA-Lip-TR | 7.4 | 143.10 ± 0.42 | 0.17 ± 0.17 | −37.82 ± 1.15 |
| pH = 6.0 PGA-Lip-TR | 6.0 | 103.75 ± 1.96 | 0.23 ± 0.01 | 25.42 ± 5.52 |
| SLN-T | 7.4 | 143.20 ± 1.86 | 0.17 ± 0.05 | 17.91 ± 1.66 |
| pH = 7.4 PGA-SLN-T | 7.4 | 192.30 ± 3.41 | 0.16 ± 0.02 | −43.53 ± 0.50 |
| pH = 6.0 PGA-SLN-T | 6.0 | 141.71 ± 1.75 | 0.24 ± 0.01 | 20.10 ± 1.99 |

$^a$PDI, polydispersity index

Example 8. pH-Sensitive Release of Drug and miR

Different formulations were incubated at 25° C. for the predetermined time intervals. At the indicated time, a dispersion of Oxa or miR contained nanoparticles was centrifuged through an ultracentrifuge filter for 30 min. Then, the filtrate Oxa- or miR was collected and analyzed by UV/VIS Spectrophotometer (Biochrom, Massachusetts, USA) and NanoDrop (Thermo Fisher, Massachusetts, USA), respectively.

Example 9. Cell Culture

Normal human oral keratinocyte NOK cells and rat small intestine epithelial IEC-6 cells were incubated in Dulbecco's modified Eagle's medium (DMEM) supplemented with 10% fetal bovine serum and insulin. HCT116 cells, HeLa cells and SAS cells are human colorectal cancer, human cervical cancer and human tongue squamous cell carcinoma cell lines. These cells were cultured in Dulbecco's modified Eagle's medium (DMEM) supplemented with 10% fetal bovine serum.

Example 10. Cellular Uptake

Peptide-conjugated and daunorubicin-loaded liposomes (Lip-TR/DNR) and FAM-miR-320 loaded SLN (SLN/FAM-miR-320) were used to quantitate the cellular uptake in HCT116 cells. Cells were seeded in 24-well plates. After the incubation of Lip-TR/DNR or SLN/FAM-miR-320 for 24 h, collected cell pellets were washed with PBS and re-suspended in 1 mL PBS buffer. The fluorescent intensity of Lip-TR/DNR or SLN/FAM-miR-320 took up by cells was measured by flow cytometer (BD Biosciences, San Jose, Calif., USA) equipped with an argon ion laser and operated at 488 nm. Red DNR fluorescence was measured through a 585/42 nm band pass filter. Data acquisition and analysis were performed using CELL Quest (BD Biosciences, San Jose, Calif., USA). Within each experiment, determinations were performed in triplicate.

Figures 3C, 3D:
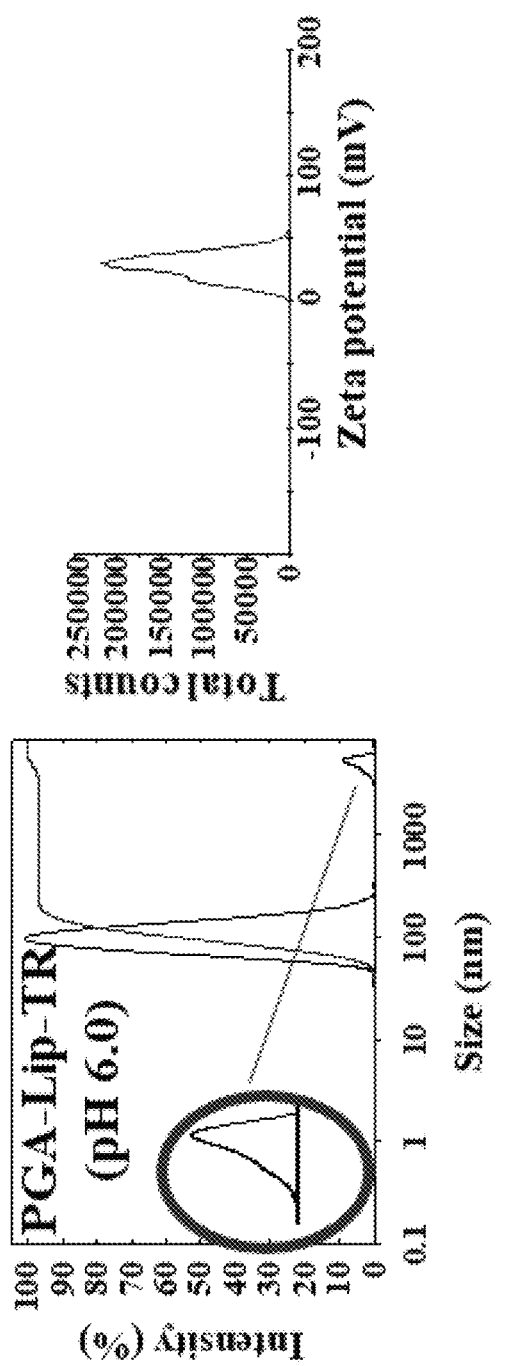
Figures 3G, 3H:
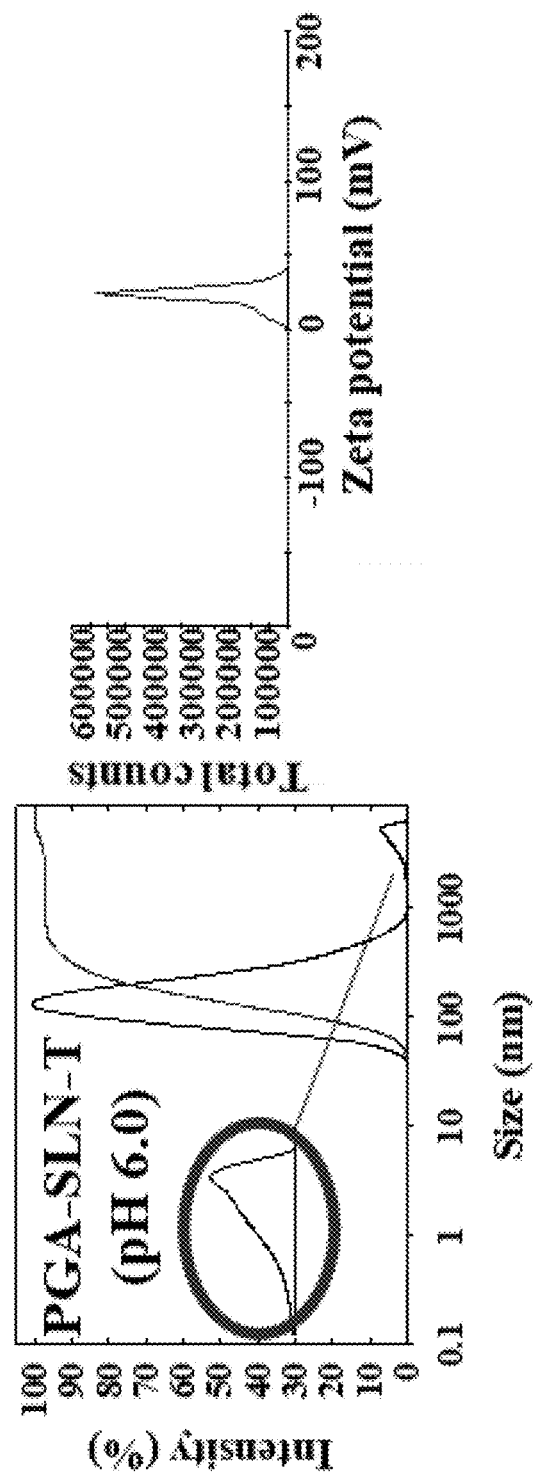
Figure 3I:
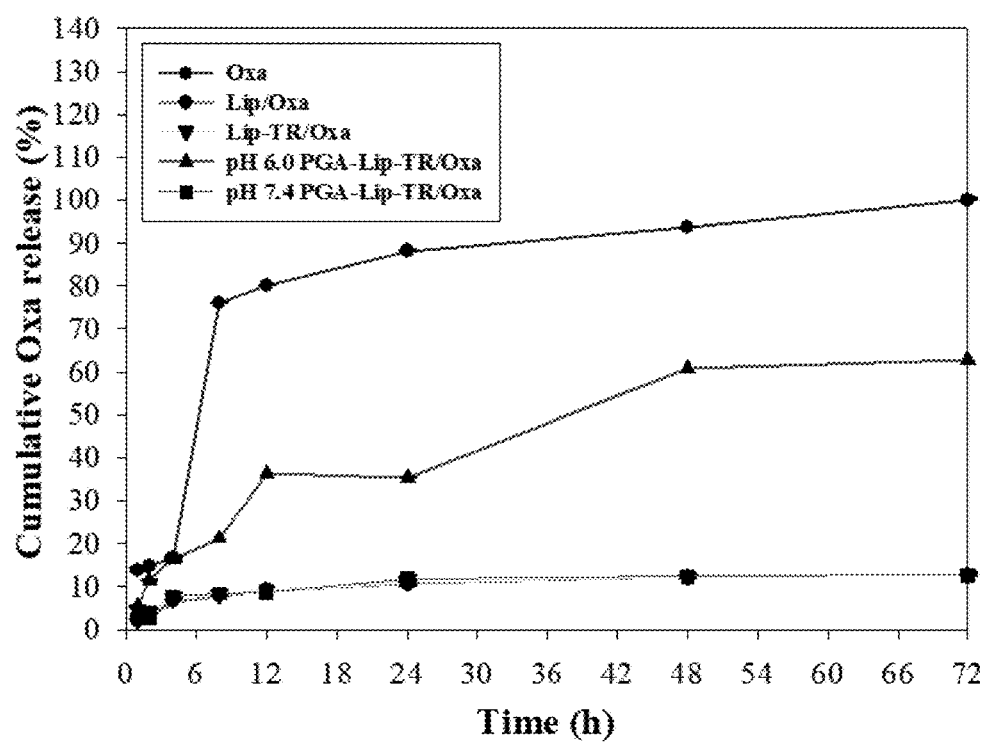
FIG. 3I shows the release profiles of Oxa formulations measured by spectrophotometer after incubating with pH 7.4 or pH 6.0 PBS at 37° C. for 72 h. PGA coating escalated the pH-sensitive Oxa release of PGA-Lip-TR/Oxa at pH 6.0.
Figure 3J:
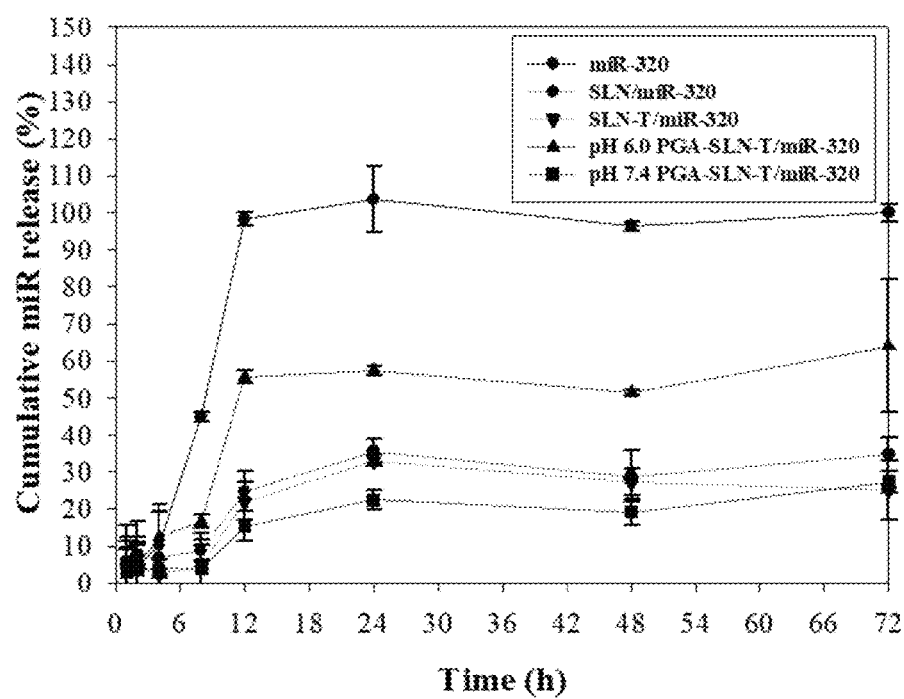
FIG. 3J shows the release profiles of miR-320 formulations measured by spectrophotometer after incubating with pH 7.4 or pH 6.0 PBS at 37° C. for 72 h. PGA coating increased the pH-sensitive miR release of PGA-SLN-T/miR-320 at pH 6.0.
Figures 3K, 3L:
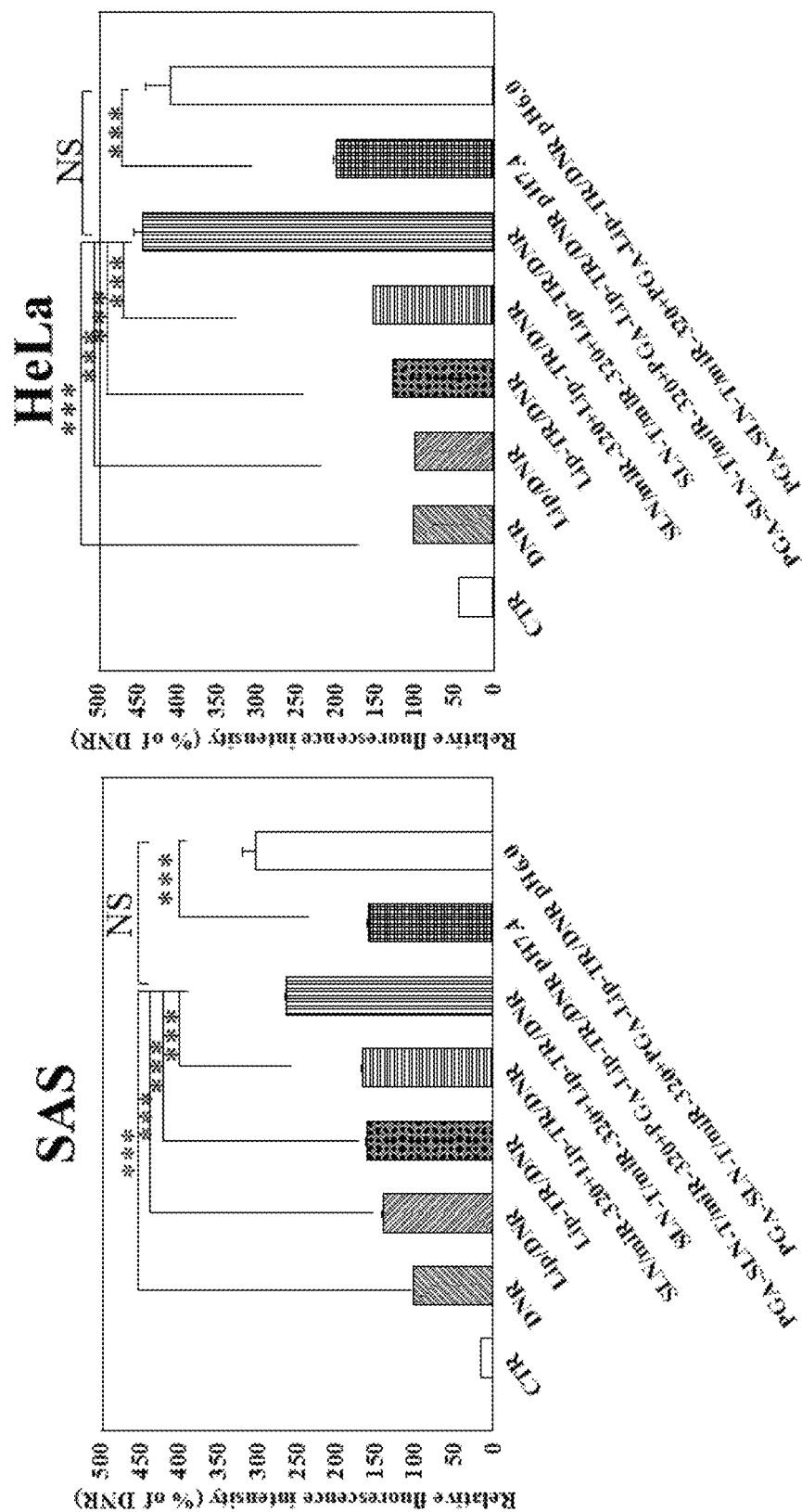
FIG. 3K-3M shows the cellular uptake of daunorubicin (DNR; a fluorescent probe of Oxa; red color) in various formulations into SAS, NUGC3, and HeLa cells, as measured by flow cytometry after incubating with pH 7.4 or pH 6.0 DMEM for 24 h. ***P<0.001. The results are shown as mean standard deviation (mean SD) from three independent experiments. The pH-shiftable de-coating of PGA shell exposed the inner peptide T and R to enhance the uptake of Lip into cancer cells.
Figure 3M:
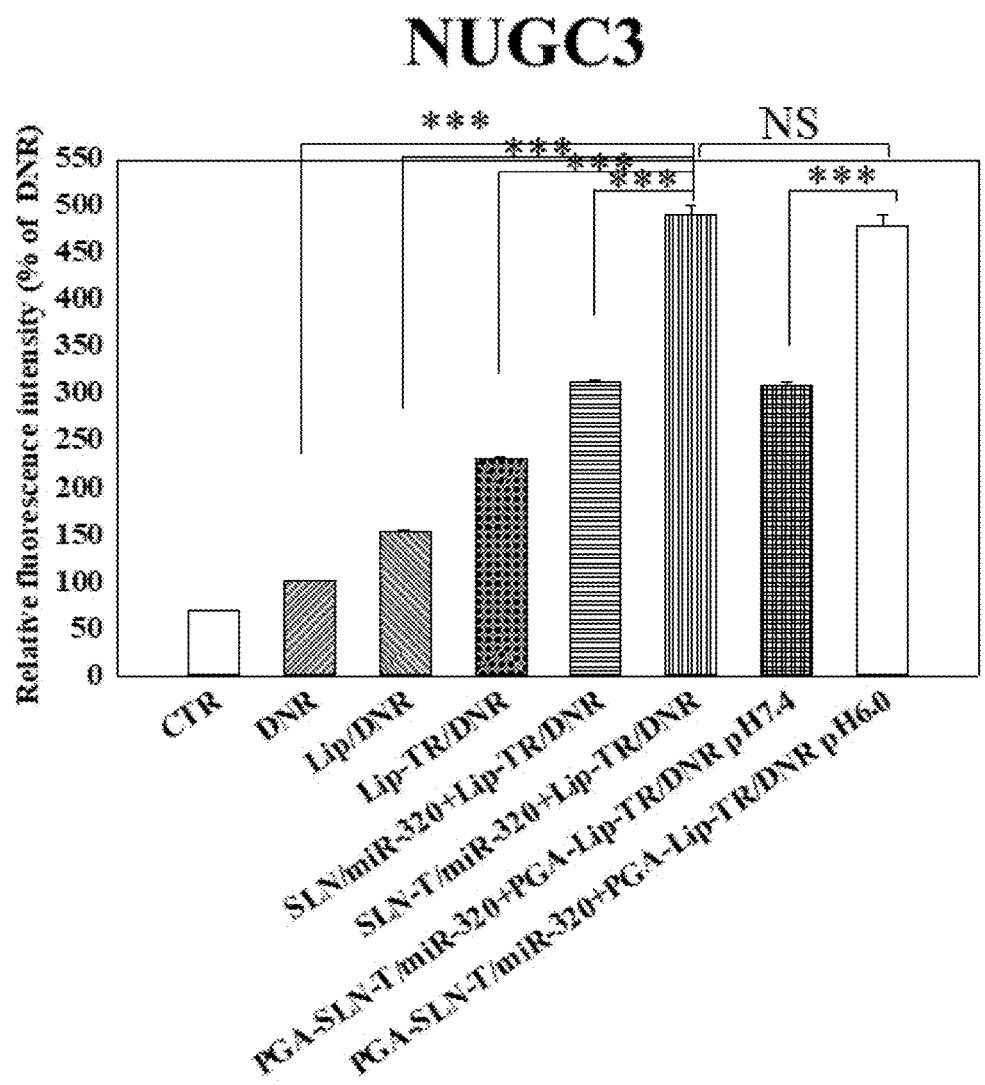
Figures 3N, 3O:
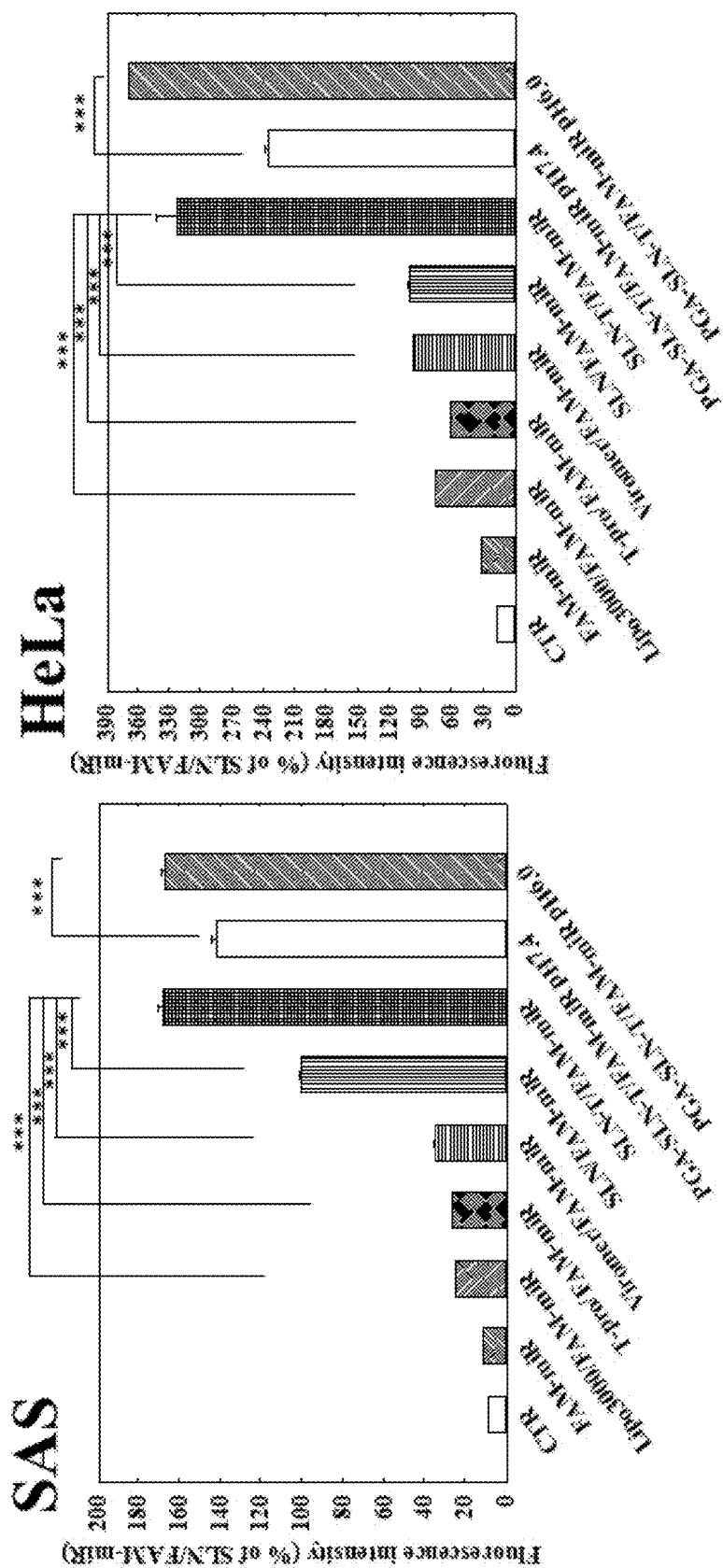
FIG. 3N-3P shows the transfection efficiency of FAM-miR-320 (green color) in various formulations into SAS, NUGC3, and HeLa cells measured by flow cytometry after incubating with pH 7.4 or pH 6.0 DMEM for 24 h. ***P<0.001. The results are shown as mean SD from three independent experiments. The pH-shiftable de-coating of PGA shell exposed the inner peptide T to enhance the uptake of SLN into cancer cells.
Figure 3P:
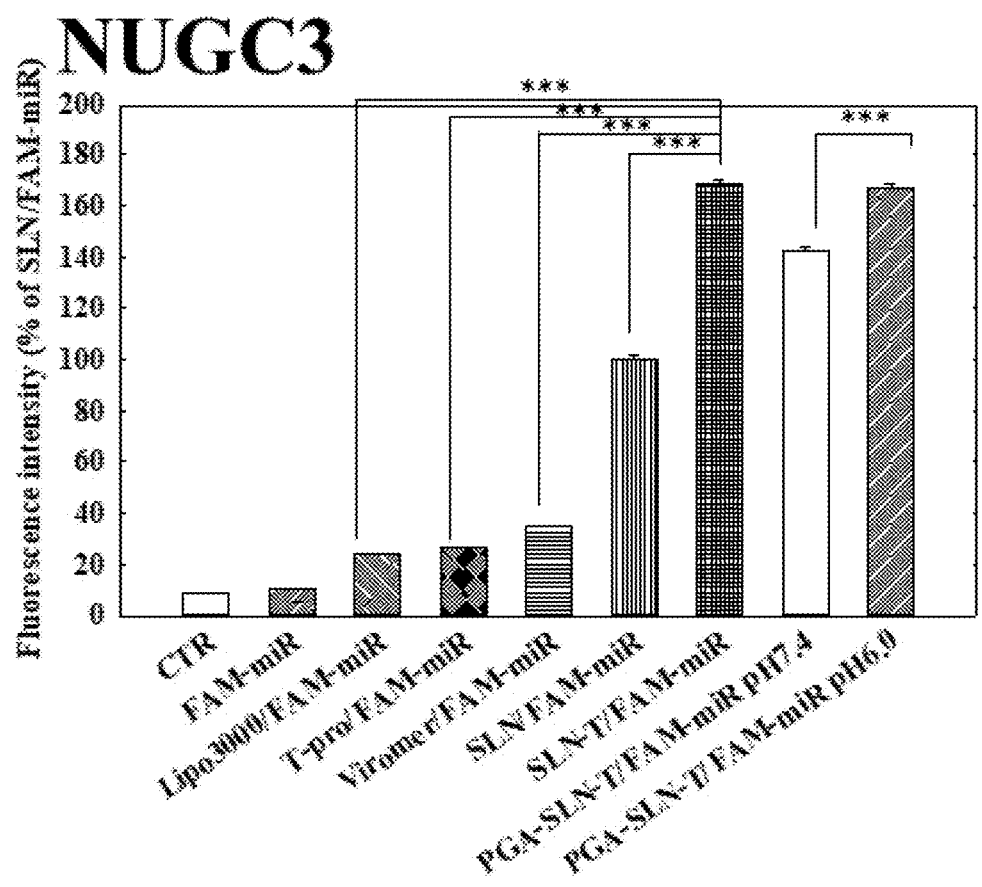

The cellular uptake of daunorubicin (DNR; a fluorescent probe of Oxa; red color) in various formulations into SAS, NUGC3, and HeLa cells were measured by flow cytometry after incubating with pH 7.4 or pH 6.0 DMEM for 24 h (FIG. 3G-3I). ***$P<0.001$. The results are shown as mean±SD from three independent experiments. SLN/miR-320 and Lip-TR/DNR significantly increased the intracellular accumulation of DNR compared to those of DNR with or without Lip encapsulation (FIG. 3N-3P; all $P<0.001$). The cellular uptake of PGA-SLN/FAM-miR-320 and PGA-Lip-TR/DNR were considerably decreased compared to that of SLN/miR-320 and Lip-TR/DNR at pH 7.4 (Figure Q; $P<0.001$), indicating the hindrance of cellular uptake by PGA-PEG shell. On the contrary, the cellular uptake of co-treatment of PGA-SLN/miR-320 and PGA-Lip-TR/DNR at pH 6.0 showed no significant difference compared to that of SLN/miR-320 and Lip-TR/DNR (FIG. 3R; $P>0.05$), suggesting that PGA-coated formulations might function as tumor microenvironment-responsive nanoparticles. The pH-sensitive de-coating of PGA shell at pH 6.0 exposed the inner peptide T and R to enhance the uptake of DNR at acidic tumor sites in SAS, NUGC3, and HeLa cells (FIG. 3K-3M).

Example 11. MicroRNA Transfection Study $1\times10^5$ cells per well were seeded into 24-well plates in DMEM containing 10% FBS and 1% penicillin/streptomycin for 24 h. SLN/FAM-miR-320 T-Pro/miR-320, Viromer/miR-320 and Lipofectaminem 3000/miR-320 with the miRNA concentration of 100 nM were added to the cells and further incubated for 24 h. Cells were collected and resuspended in 1 mL cold PBS buffer. The amount of FAM-miR-320 taken up by cells were measured by flow cytometer (BD Biosciences, San Jose, Calif., USA) equipped with an argon ion laser and operated at 488 nm. Green FAM fluorescence was measured through a 530/30 nm band pass filter. Data acquisition and analysis were performed using CELLQuest (BD Biosciences, San Jose, Calif., USA). Forward- and side-scatter signals were collected using linear scales, and fluorescence signals were collected on a logarithmic scale. At least $1\times10^4$ cells were analyzed in each sample. Within each experiment, determinations were performed in triplicate. Mean fluorescence intensity of SLN/FAM-miR-320 group was normalized as 100%. Mean fluorescence intensity of FAM-miR-320, T-pro/FAM-miR-320, Viromer/FAM-miR-320, Lipofectamine-3000/FAM-miR-320 or SLN/FAM-miR-320 was normalized relative to SLN/FAM-miR-320. Data are means SD of three independent experiments.

The relative transfection % of FAM-miR-320 in various formulations into SAS, NUGC3, and HeLa cells were measured by flow cytometry after incubating with pH 7.4 or pH 6.0 DMEM for 24 h (FIG. 3N-3P). ***$P<0.001$. The results are shown as mean SD from three independent experiments. As shown in FIG. 3G-3H, the relative transfection % of FAM-miR-320 in SLN-T was greater than those of many commercial transfection reagents, including T-pro, Viromer® and Lipofectamine™ 3000. SLN-T could compact miRNA into a condensed structure and thus prevent miRNA from degradation by nuclease. Furthermore, the positively-charged SLN-T assisted miRNA in endosomal escape and thus displayed remarkable transfection improvement (FIG. 3N-3P).

Example 12. Identification of Intracellular Localization

To observe the intracellular localization of Lip-TR/DNR and SLN-T/FAM-miR-320 in SAS cells, the cells were seeded in 24-well plates. After incubating with Lip-TR/DNR or SLN/FAM-miR-320, cells were stained with LysoTracker® Green/Red to identify lysosomes before they were fixed in 4% paraformaldehyde. The fixed cells were studied using immunofluorescence staining to recognize the early endosomes (by antibody against Early Endosome Antigen 1; EEA1). The cells were also counterstained using DAPI to visualize the nuclei. The images were taken using a confocal laser scanning microscope (CLSM, FV10i, OLYMPUS, Tokyo, Japan).

Figure 3Q:
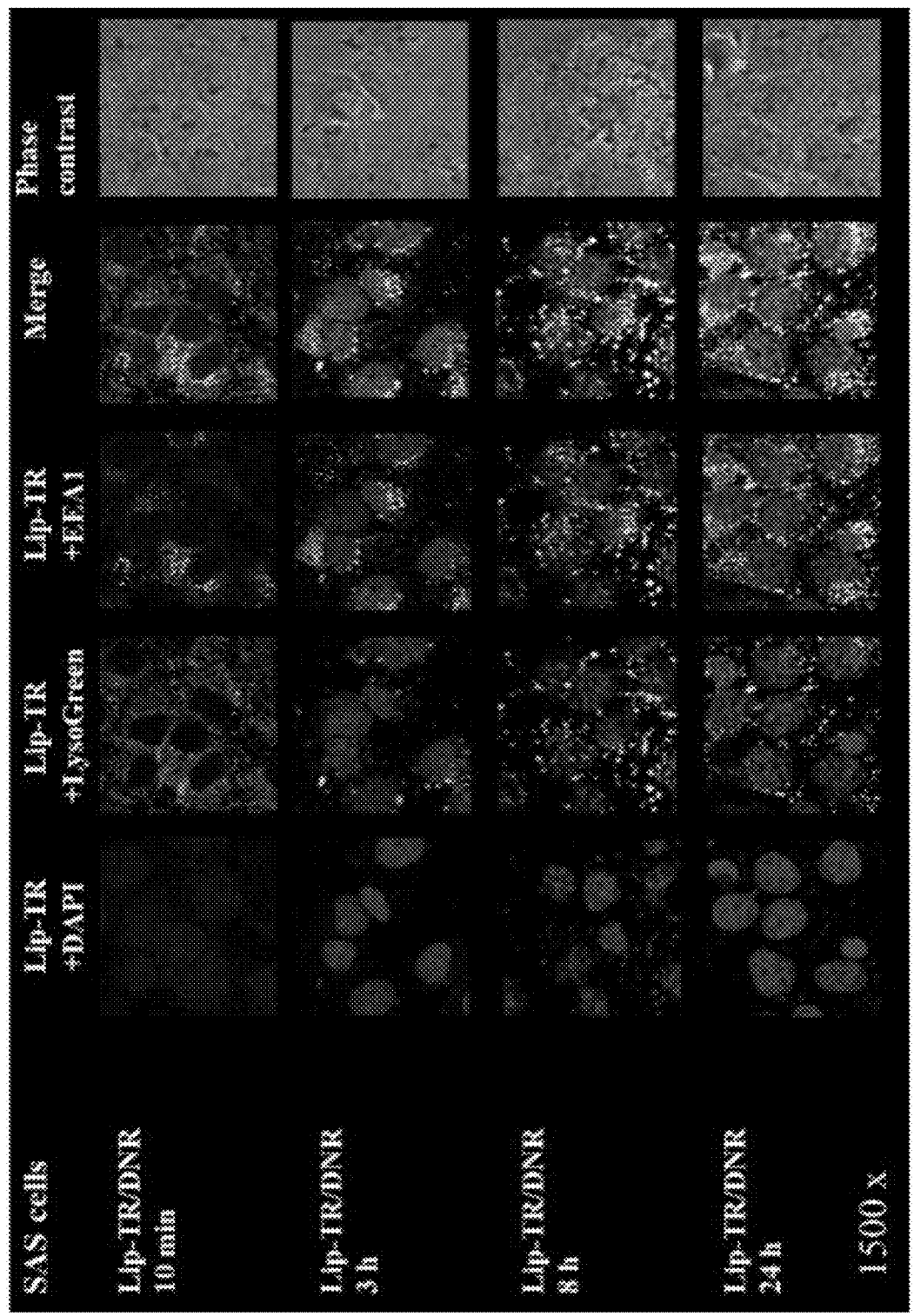
FIG. 3Q shows the nuclear targeting of Lip-TR/Oxa in SAS cells by CLSM [DNR: DAPI: a nuclear dye; LysoGreen (LysoTracker Green): a lysosomal dye; EEA1 (early endosome antigen 1): an early endosome marker]. The pH-responsive de-coating of PGA shell exposed the inner peptide T and R to enhance the uptake of Lip into cancer cells (FIGS. 3E,3F 3I,) thus improving endosomal escape of these nanoparticles to release Oxa at the intracellular target site of the nucleus (FIG. 3Q).

The result of nuclear targeting of Lip-TR/Oxa in SAS cells by CLSM is shown in FIG. 3Q. DNR: a fluorescent probe of oxaliplatin; DAPI: a nuclear dye; LysoGreen (LysoTracker Green): a lysosomal dye; EEA1 (early endosome antigen 1): an early endosome marker. The result suggested that at 10 min and 3 h, Lip-TR/DNR was mainly located in early endosomes (stained with cyan-labeled anti-EEA1 antibody). However, at 8 h, Lip-TR/DNR (red) were mainly localized in the nucleus and not co-localized with early endosomes (stained with grey anti-EEA1 antibody), but still showed a slight co-localization with lysosomes (stained green with LysoGreen), as displayed in FIG. 3Q. Excitingly, at 24 h after incubation, DNR (red) released from Lip-TR was distributed principally in the nucleus. Consequently, Lip-TR exhibited good endosomal escape capability to prevent DNR from degradation in lysosomes and reached the intracellular target site of the nucleus (FIG. 3Q).

Figure 3R:
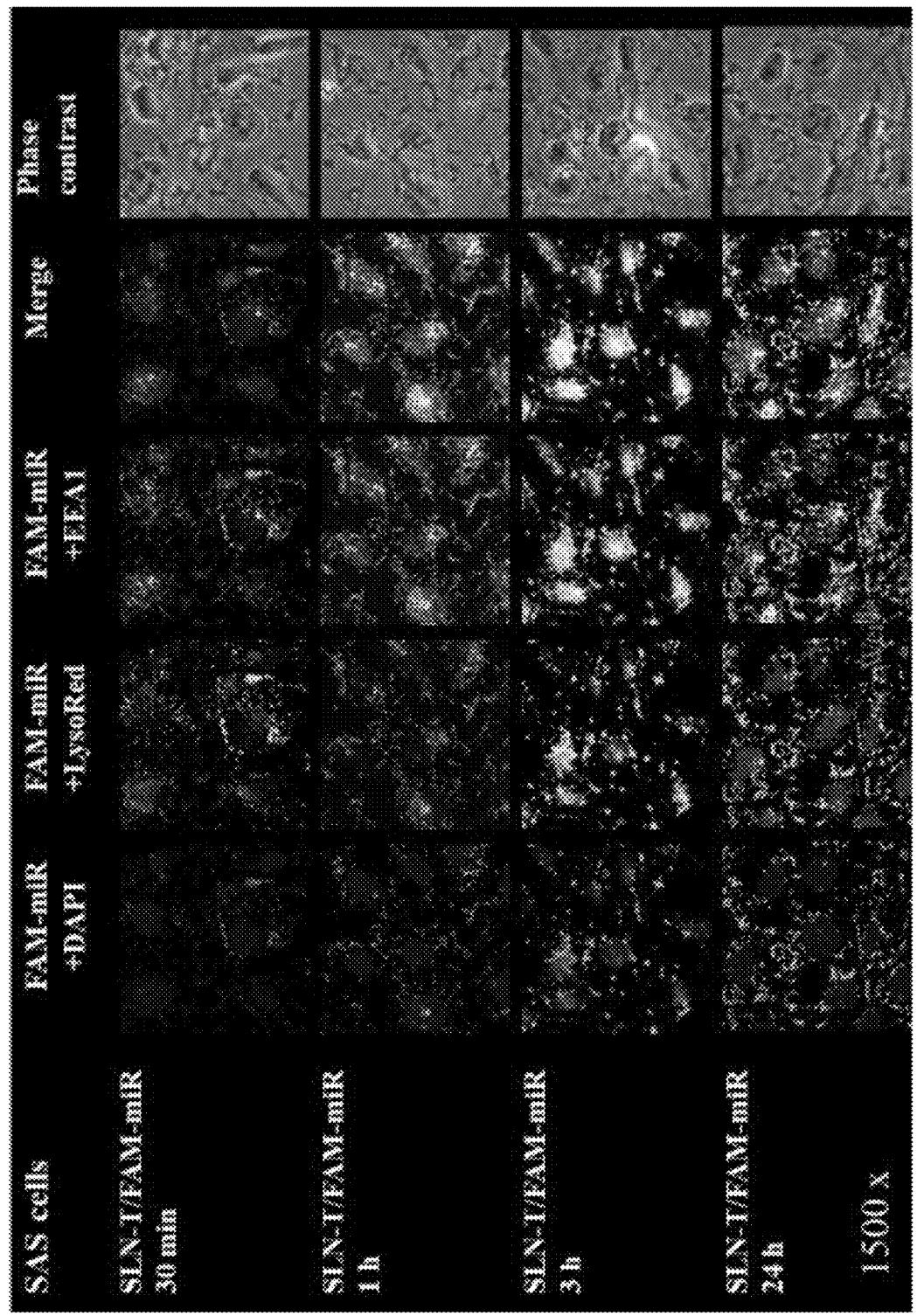
FIG. 3R shows the cytoplasmic localization of SLN-T/FAM-miR-320 in SAS cells by CLSM [DNR: DAPI: a nuclear dye; EEA1 (early endosome antigen 1): an early endosome marker; LysoRed (LysoTracker Red): a lysosomal dye]. The pH-sensitive de-coating of PGA shell exposed the inner peptide T to increase the uptake of SLN into cancer cells (FIG. 3G,3H,3J), thus improving endosomal escape of these nanoparicles to release miR at the intracellular target site of the cytoplasm (FIG. 3J).

The result of cytoplasmic localization of SLN-T/FAM-miR-320 in SAS cells by CLSM is shown in FIG. 3R. DAPI: a nuclear dye; EEA1 (early endosome antigen 1): an early endosome marker; LysoRed (LysoTracker Red): a lysosomal dye. The green fluorescence of FAM-miR-320-loaded SLN-T was co-localized with early endosomes (stained with cyan-labeled anti-EEA1 antibody) in SAS cells after 1 h-incubation. At 3 h after transfection, the major portion of FAM-miR-320 (green) delivered by SLN-T was distributed to the cytoplasm with a small portion in lysosome, as indicated by the yellow color of co-localization of green FAM-miR and lysosomes (stained red with LysoRed; FIG. 3R). Nonetheless, at 24 h after transfection, FAM-miR-320 released from SLN-T was predominately localized in the cytoplasm and merely not co-localized with early endosomes and lysosomes (FIG. 3R). As a result, SLN-T exhibited good endosomal escape capability to prevent miR-320 from degradation in lysosomes and reached the intracellular target site of the cytoplasm (FIG. 3R).

Example 13. Hemolysis Assay $7\times10^7$ RBCs from rat were separated by centrifugation of whole blood. The supernatant containing plasma and platelets were removed. The pellets were washed by PBS until the supernatant was clear. Different formulations were diluted to a required concentration and added to the tubes containing 1 mL diluted RBCs. The cell suspension was mixed gently and incubated at 37° C. for 24 h. Triton X-100 was served as a positive control. Hemoglobin released from RBCs was measured spectrophotometrically. The concentration of the formed product was measured at 540 nm using an ELISA reader (TECAN, Mannedorf, Switzerland) to qualify the toxicity of liposomes to RBCs.

Figure 4A:
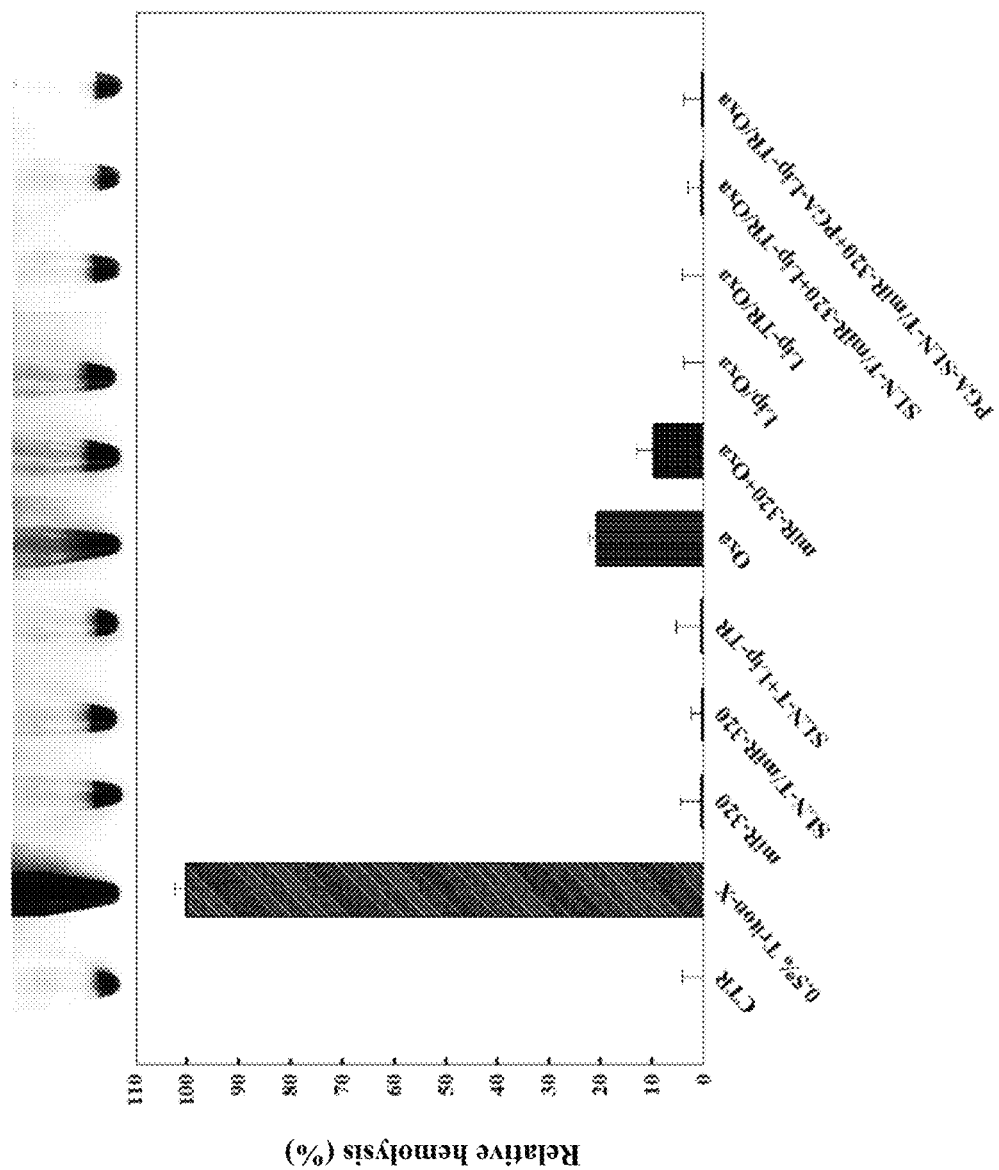
FIG. 4A shows that Oxa or Oxa+ miR displayed mild hemolysis (10~20%) compared to Triton X (100%). No hemolysis was detected for other groups, indicating the safety of PGA-SLN/miR-320 and PGA-Lip-TR/Oxa by IV injection.

The Oxa or Oxa+ miR displayed mild hemolysis (10~20%) compared to Triton X (100%). No hemolysis was detected for other groups, indicating the safety of PGA-SLN/miR-320 and PGA-Lip-TR/Oxa by IV injection (FIG. 4A).

Example 14. Cell Viability Assay: SRB Assay $5 \times 10^3$ IEC-6, NOK, HCT116, SAS and HeLa cells per well were seeded in 96-well plates in DMEM containing 10% FBS and 1% penicillin/streptomycin for overnight. The medium was then removed. DMEM with different formulations including empty liposomes (Lip-TR), empty SLNs (SLN), oxaliplatin, oxaliplatin loaded liposomes (Lip/Oxa), peptide-conjugated and oxaliplatin-loaded liposomes (Lip-TR/Oxa) and miR-320 loaded SLN (SLN/miR-320) were added. After incubation at 37° C. for 48 h, medium was removed, and 1% TCA was added to each well at room temperature. After 1 h incubation, 0.04% SRB were added in each well for 30 min and then wash the plates three times with 1% acetic acid. After 24 h, added TRIS base into each well and measured the absorbance at 540 nm by ELISA reader (TECAN, Mannedorf, Switzerland).

Figures 4B, 4C:
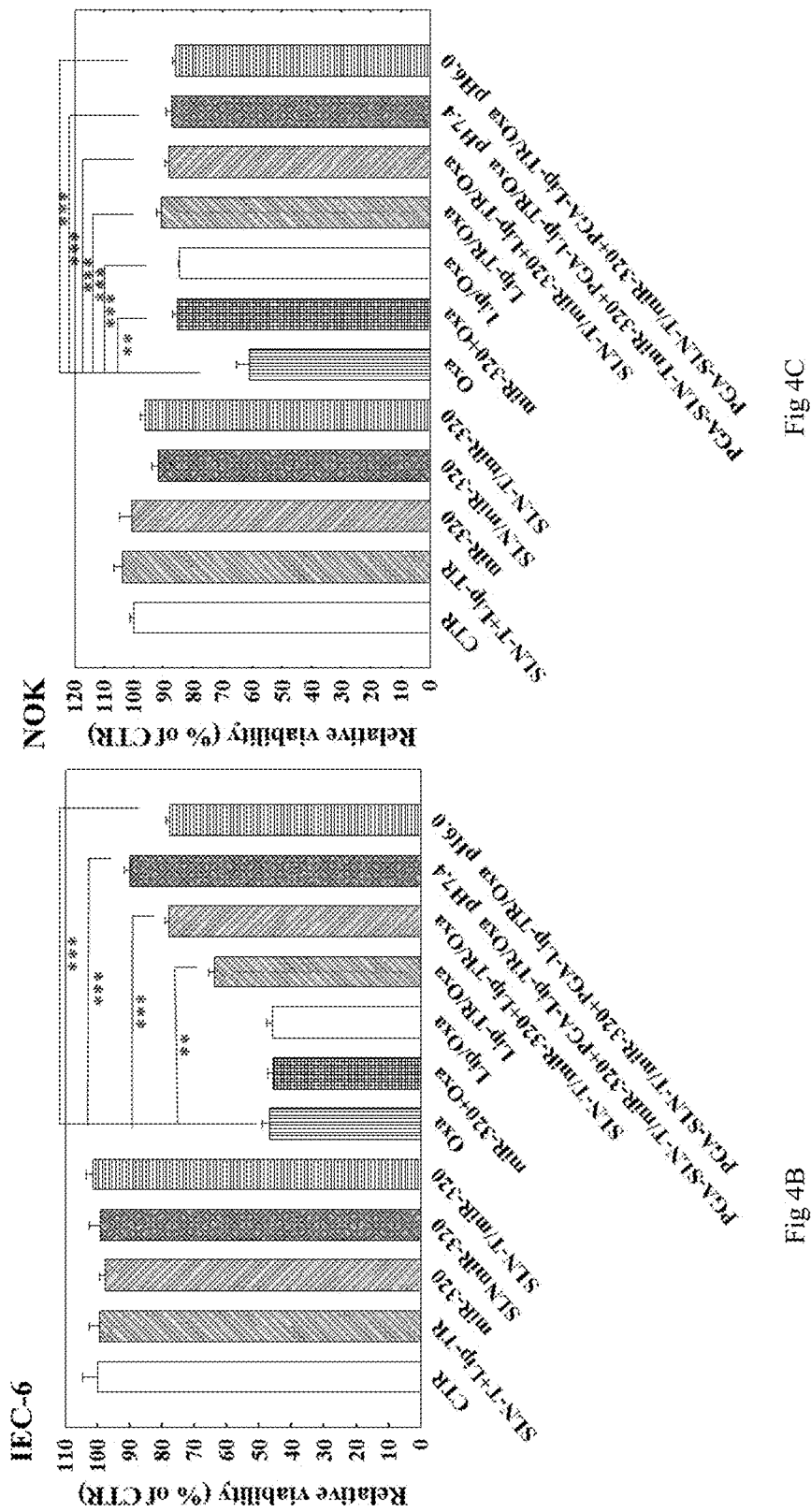
FIG. 4B , C shows that IEC-6 and NOK cells were treated with different formulations and the cell viability was measured by SRB assay. The results are presented as mean±SD.PGA-SLN/miR-320 and PGA-Lip-TR/Oxa displayed low cytotoxicity to NOK and IEC-6 cells, indicating the safety of PGA-SLN/miR-320 and PGA-Lip-TR/Oxa to normal oral and intestinal cells.
Figure 4D:
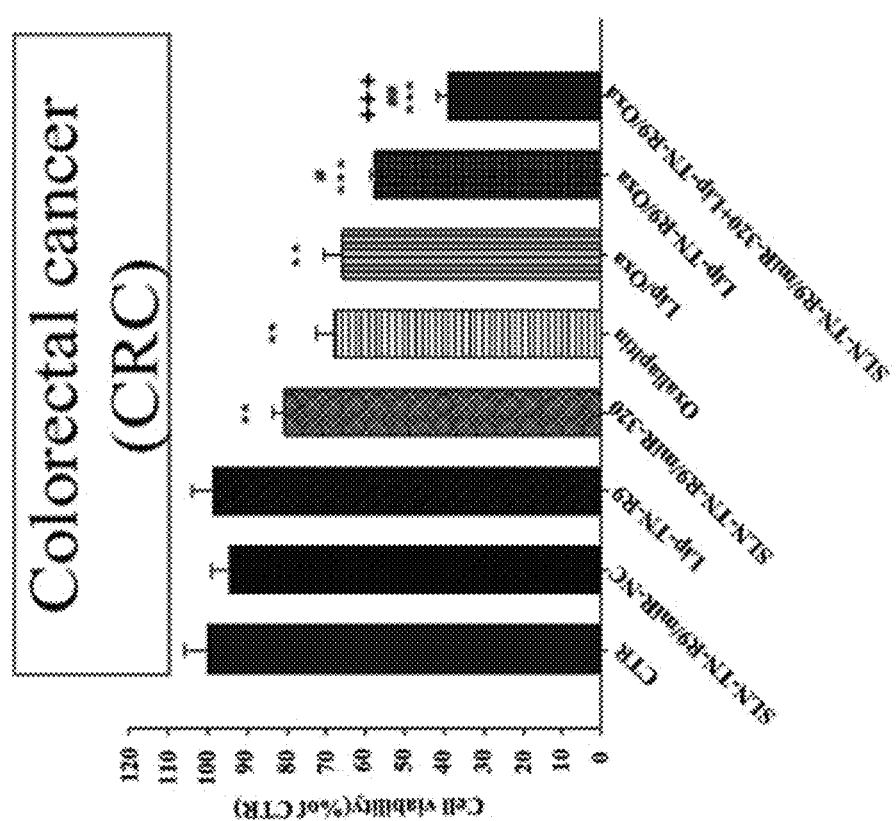
FIG. 4D-4G shows that cancerous HCT116, SAS, HeLa, and NUGC3 cells was treated with different formulations and the cell viability was measured by SRB assay. The results are presented as mean SD. PGA-SLN/miR-320 and PGA-Lip-TR/Oxa exhibited the highest cytotoxicity on various cancer cells, indicating the superior cytotoxicity of PGA-SLN/miR-320 and PGA-Lip-TR/Oxa against different cancer types.
Figure 4E:
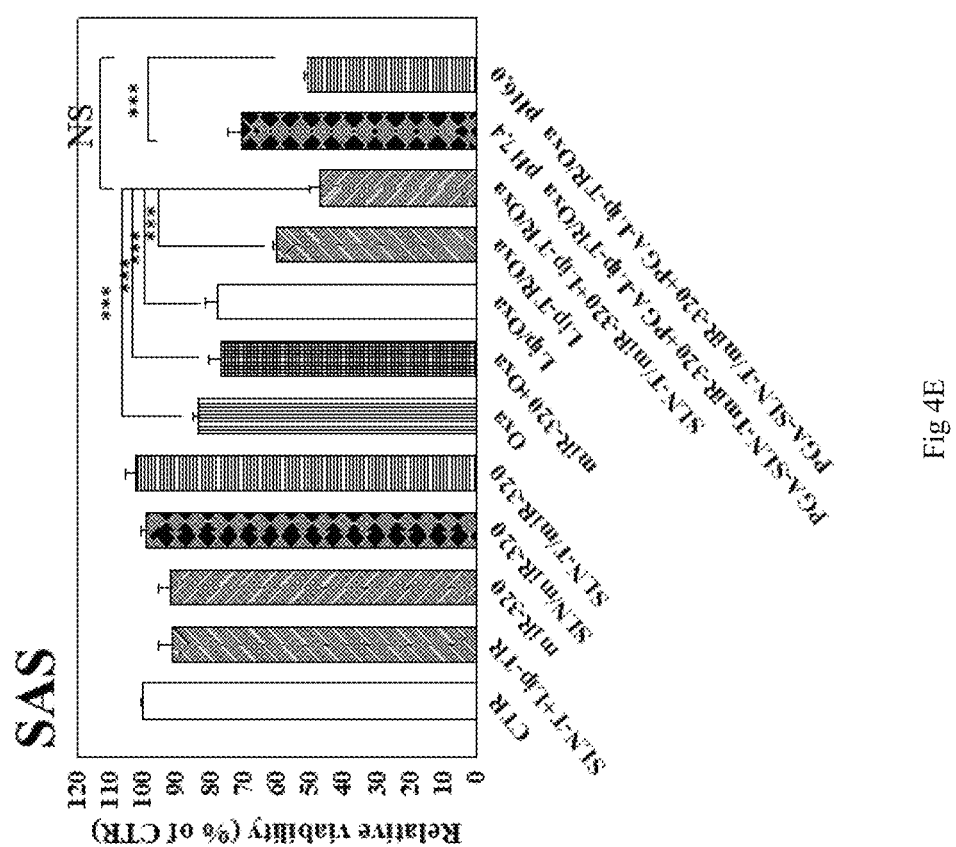
Figure 4F:
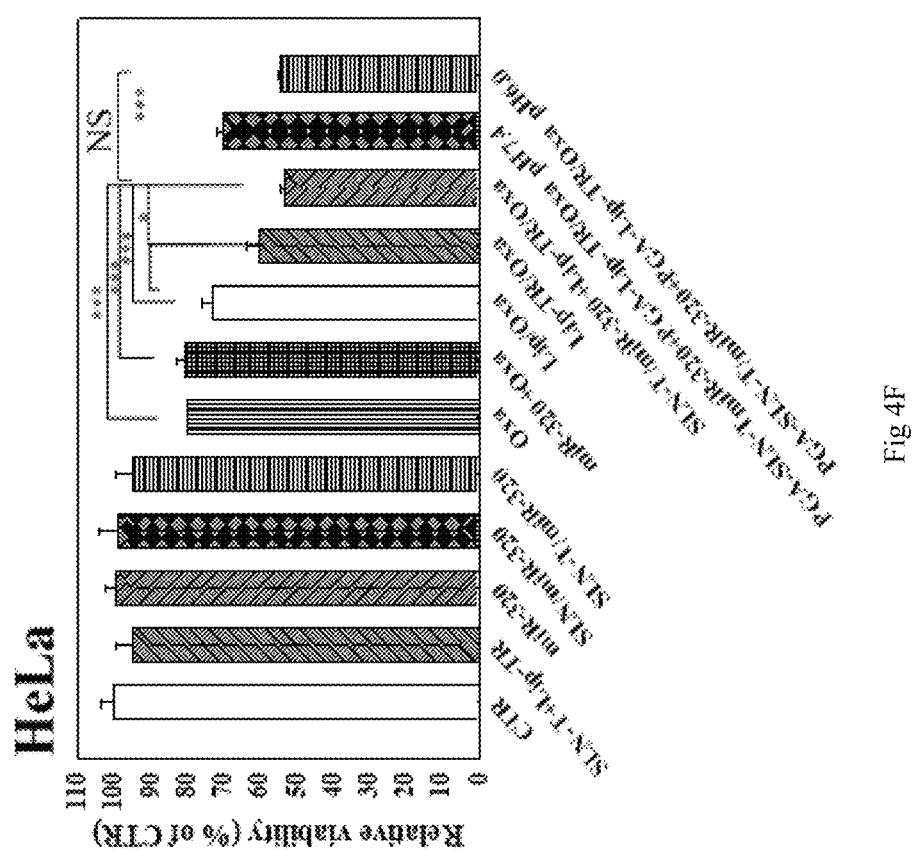
Figure 4G:
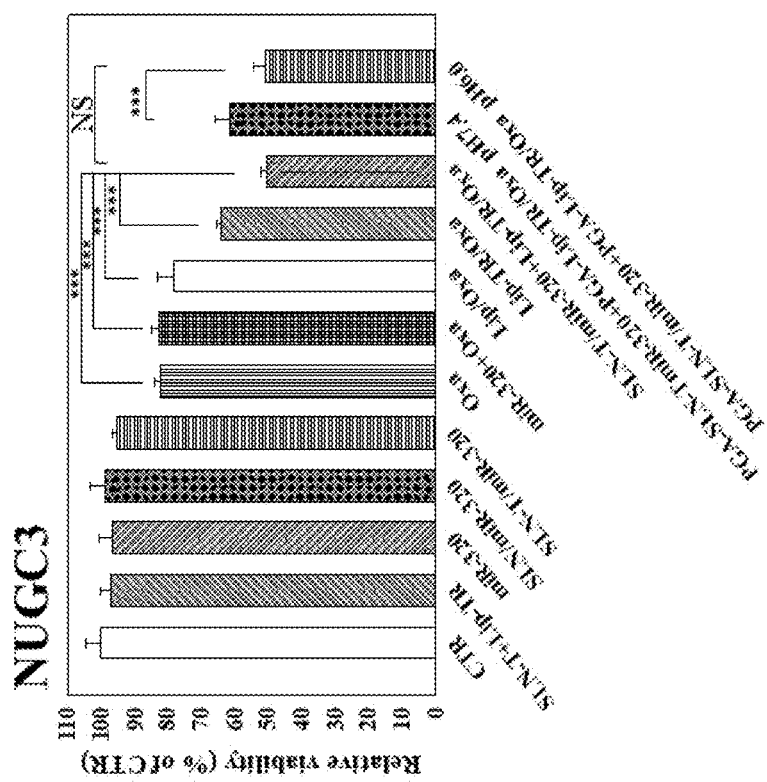

The results of viability of normal cells measured by SRB assay suggested that PGA-SLN-T/miR-320 and PGA-Lip-TR/Oxa displayed low cytotoxicity to noncancerous IEC-6 and NOK cells (FIG. 4B-4C). Furthermore, the cytotoxicity of miR-320 and Oxa-loaded formulations against SAS, HeLa, and NUGC3 cells was evaluated with SRB assay. As shown in FIG. 4D-4G, Lip-TR/Oxa exhibited more cytotoxicity than those of Lip/Oxa (all P<0.05). With the assistance of SLN-T/miR-320, Lip-TR/Oxa exhibited more reduction on viability of the tested 3 cancer cell types (FIG. 4A-4C). For all 3 cancer cell lines, PGA-SLN-T/miR-320 and PGA-Lip-TR/Oxa decreased the cell viability to the greatest extent among all the groups, especially at pH 6.0 (FIG. 4D-4G).

Example 15. Western Blot Assay

Cells were seeded in 6 cm-dishes and grown overnight. The cells were incubated with different formulations for different time. Proteins of cells were lysed by RIPA (Cell Signaling, Beverly, Mass., USA) and measured using the BCA protein assay (Thermo Fisher Scientific, Waltham, Mass., USA). Protein samples were separated with SDS polyacrylamide gel (SDS-PAGE) and transferred onto the PVDF membranes (Bio-Rad, Hercules, Calif., USA). After blocking non-specific binding, blots were incubated overnight at 4° C. with primary antibodies, followed by conjugation with horseradish peroxidase (HRP)-conjugated immunoglobulin G (Ig G) (Jackson ImmunoResearch Inc, PA, USA). Finally, blots were visualized with enhanced chemiluminescence (ECL) kits (Millipore, Billerica, Mass., USA).

Effect of different treatments of miR-320 and/or Oxa formulations on protein expression levels of multidrug resistance (MDR) pathway in HCT116, HeLa, SAS and NUGC3 cells. The cells were pretreated with SLN-T/miR-320 and then treated with Oxa, Lip/Oxa or Lip-TR/Oxa. The protein expressions in the respective cells were evaluated by western blot.

Figures 5A, 5B, 5C:
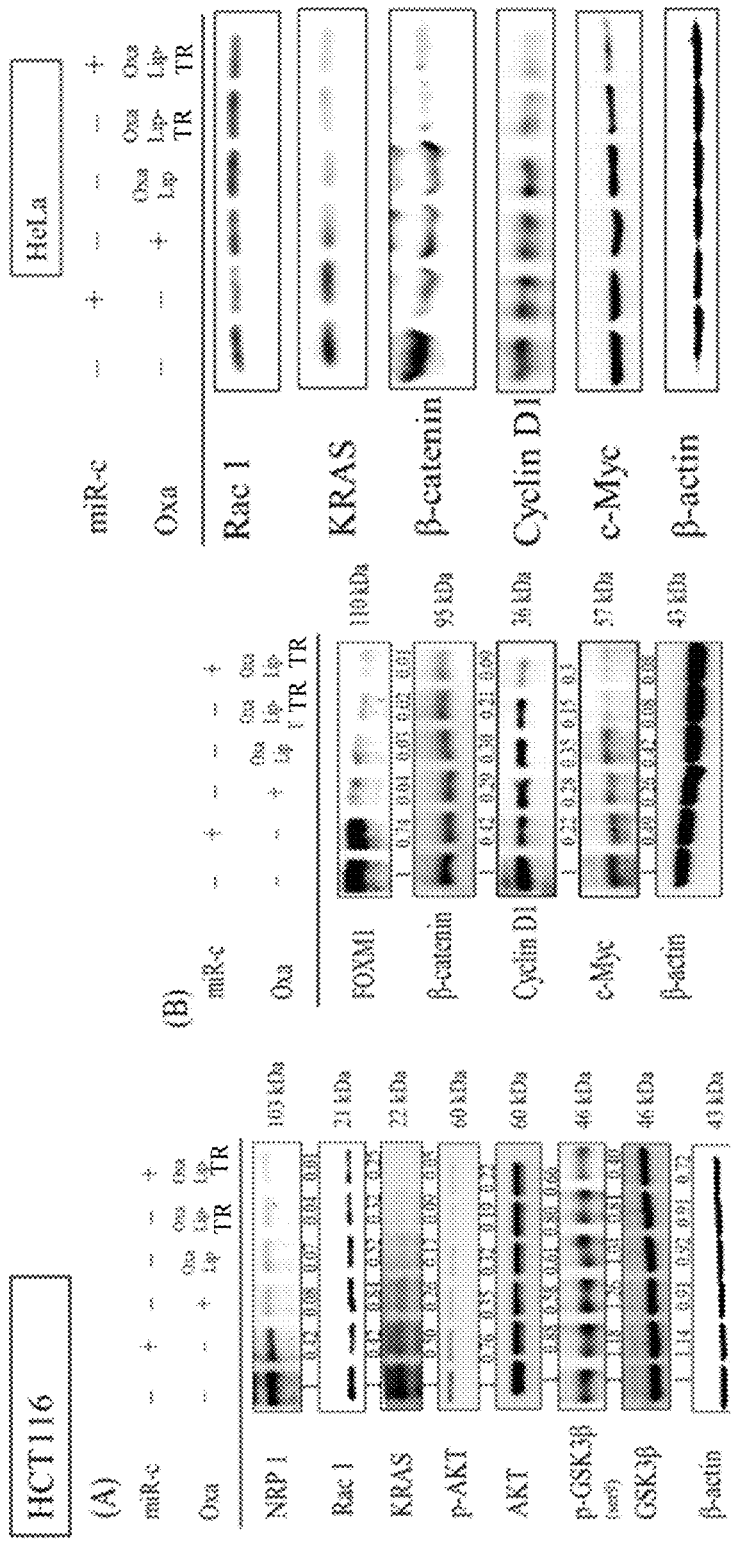
FIG. 5A-5E shows the effect of different treatments of miR-320 and/or Oxa formulations on protein expression levels of FOXM1/β-catenin/NRP1/KRAS pathway. The co-treatment of SLN-T/miR-320 and Lip-TR/Oxa most downregulated FOXM1/β-catenin/NRP1/KRAS pathway among all the groups, revealing that this combined nanoparticle formulation might modulate multiple signaling pathways to inhibit cancer proliferation, progression, and tumor angiogenesis.
Figures 5D, 5E:
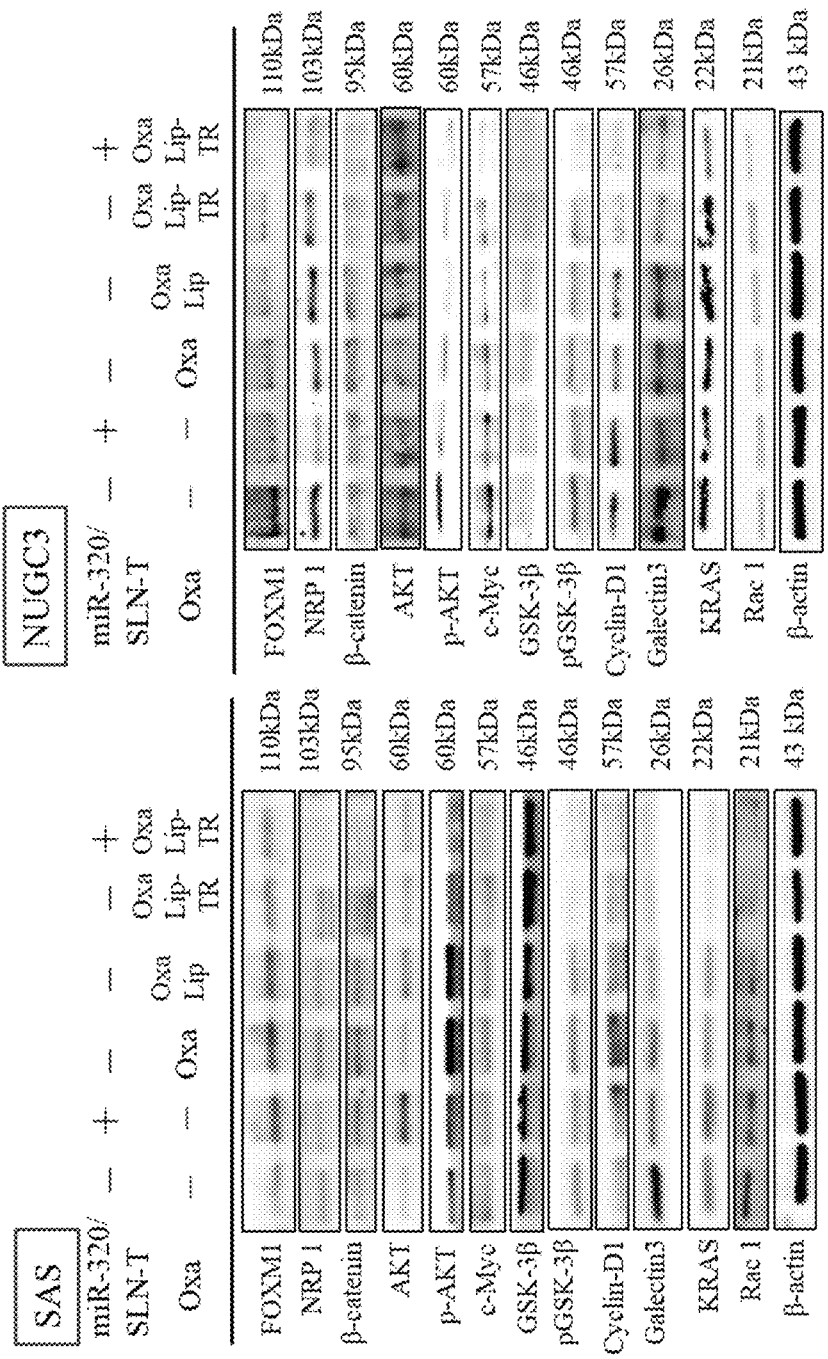
Figures 5F, 5G:
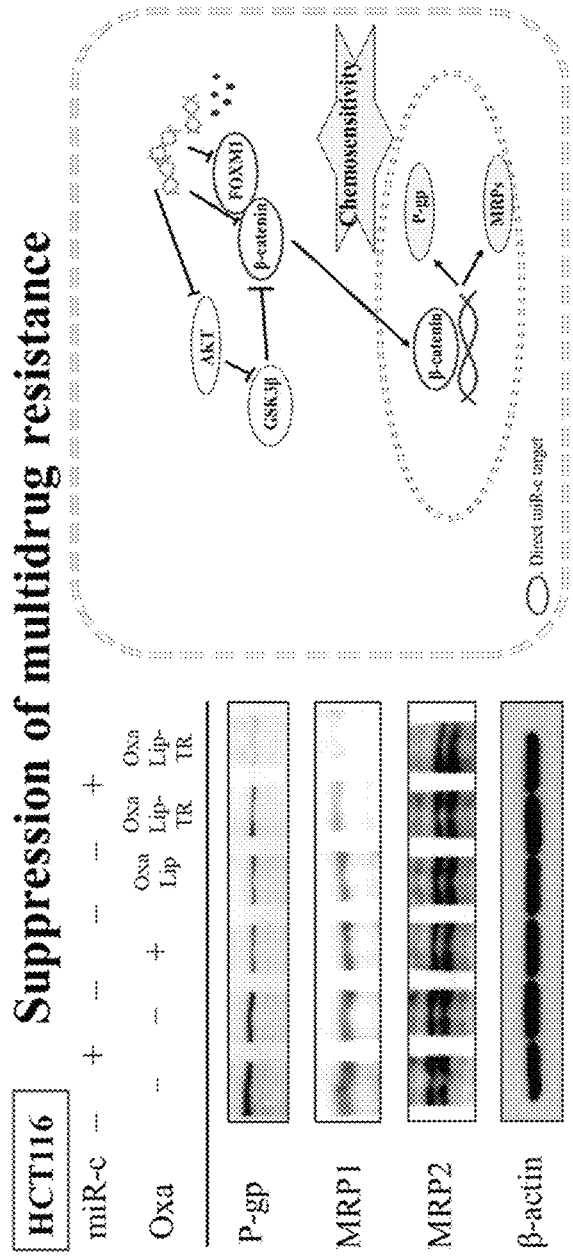
FIG. 5F-5I shows the effect of different treatments of miR-320 and/or Oxa formulations on protein expression levels of multidrug resistance (MDR) pathway in HCT116, SAS and NUGC3 cells. The combined treatment of SLN-T/miR-320 and Lip-TR/Oxa the most remarkably inhibited multidrug resistance (MDR) pathway among all the groups, suggesting that these different treatments of miR-320 and/or Oxa formulations suppressed tumor resistance to various degrees.
Figures 5H, 5I:
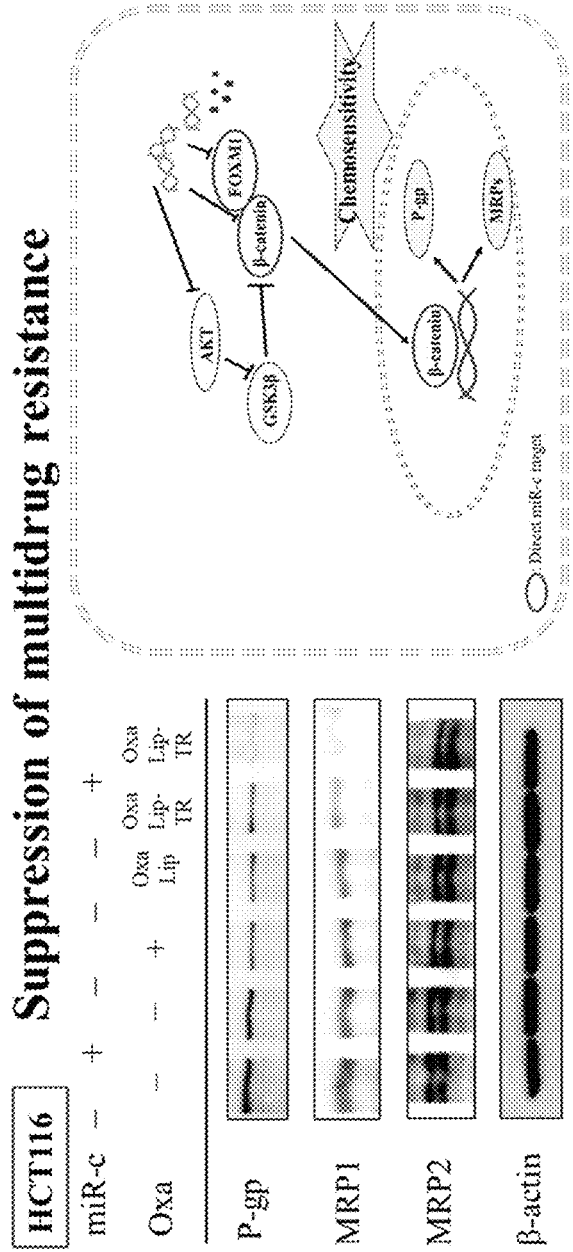

According to the result shown in FIG. 5A-5C, the protein expressions of NRP1, Rac 1, KRAS, p-AKT, p-GKS-30, FOXM1, β-catenin, Cyclin D1 and c-Myc were downregulated by the treatments of SLN/miR-320 and/or Lip-TR/Oxa, respectively. Moreover, the combination treatment of SLN/miR-320 and Lip-TR/Oxa exhibited the greatest inhibition of these proteins (FIG. 5A-5E). Furthermore, the protein expressions of P-gp, MRP1, and/or MRP 2 were downregulated in HCT116, SAS, and NUGC3 cells when the corresponding cells were treated with SLN/miR-320 and/or Lip-TR/Oxa (FIG. 5D-5E). Collectively, various treatments of SLN/miR-320 and/or Lip-TR downregulated FOXM1/β-catenin/NRP1/KRAS pathway and multidrug resistance (MDR) pathways (FIG. 5A-5I), thus inhibiting cancer proliferation, progression, tumor angiogenesis, and multidrug resistance.

Example 16. Migration Assay

HCT116 cells were seeded in Ibidi inserts (Ibidi GmbH, 81176, Munich, Germany). Once cells reached 90% confluence, the inserts were removed and different formulations were added into wells, cells were monitored for 15 hours after treatment. Migration percentage was quantified using Image J and calculated by the following equation.

Migration area (% of area at 0 h)=100%−(Blank area (15 h)/Blank area (0 h)×100%)

Figure 6A:
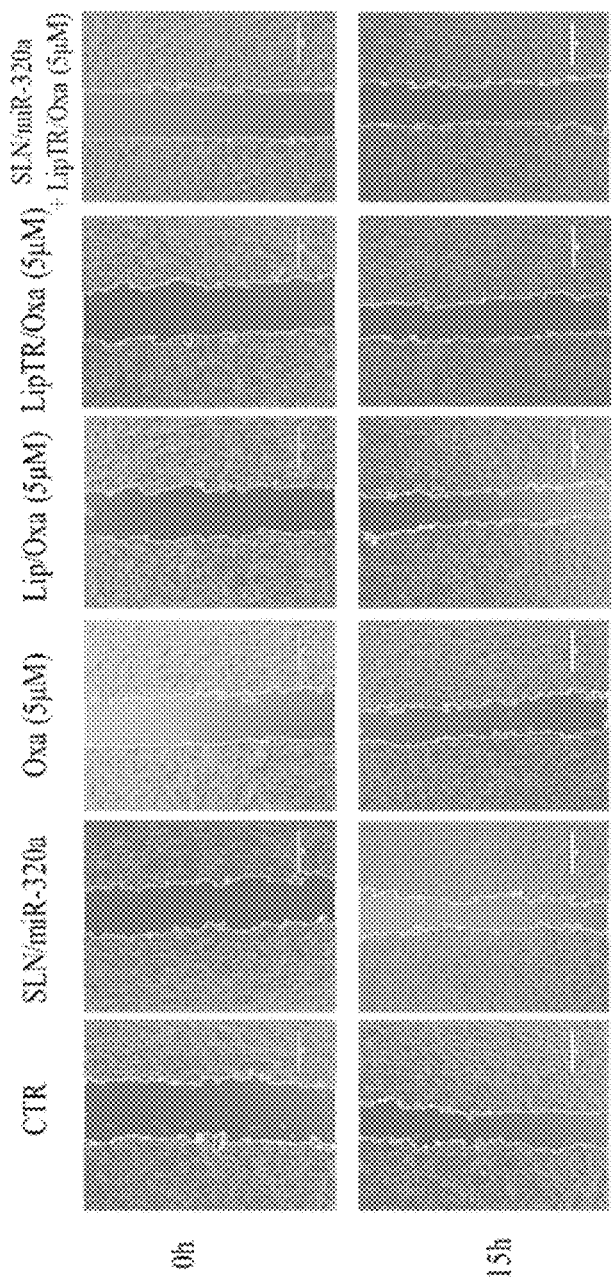
FIG. 6A-6B shows the migration images of different treatments of miR-320 and/or Oxa formulations in HCT116 cells. The cells were pretreated with SLN-T/miR-320 and then treated with Oxa, Lip/Oxa or Lip-TR/Oxa for 0 or 15 h before the migration images were taken.
Figure 6B:
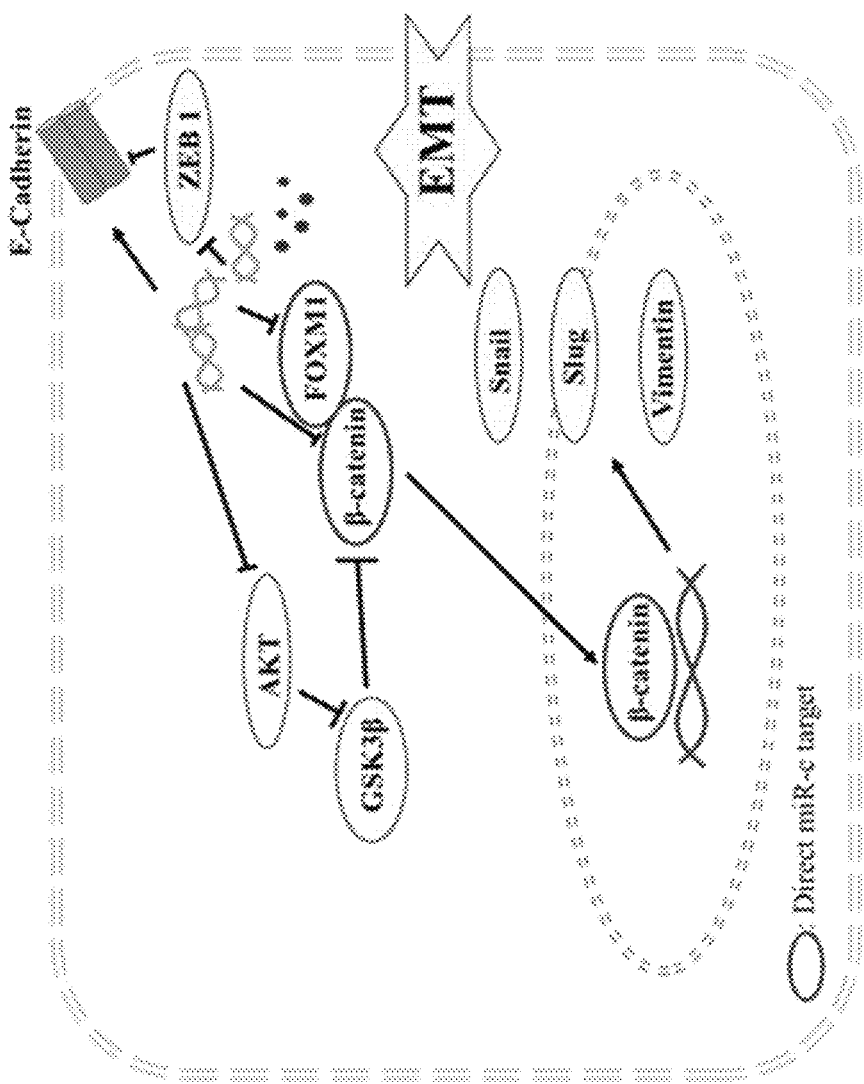

Effect of different treatments of miR-320 and/or Oxa formulations on the relative migration percentage and the EMT-associated protein expressions in HCT116 cells. The cells were pretreated with SLN-T/miR-320 and then treated with Oxa, Lip/Oxa or Lip-TR/Oxa before the migration images were taken (FIG. 6A-6B). Quantification of the relative percentage of cell migration area (FIG. 6C). P<0.01, *P<0.001 compared to CTR. ###P<0.001 compared to Lip-TR/Oxa. Western blot assay was employed to examine the expression levels of EMT-associated proteins in HCT116 cells (FIG. 6D).

Figure 6D:
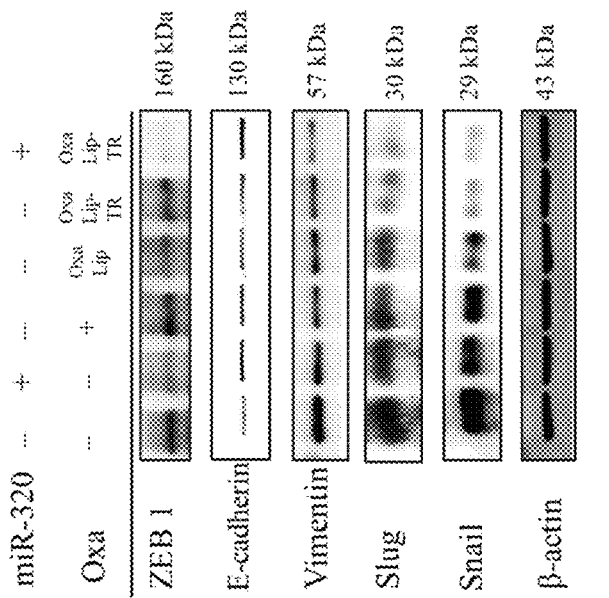
FIG. 6D shows the effect of different treatments of miR-320 and/or Oxa formulations on the epithelial-mesenchymal transition (EMT)-associated protein expressions in HCT116 cells by western blot assay.
Figure 6C:
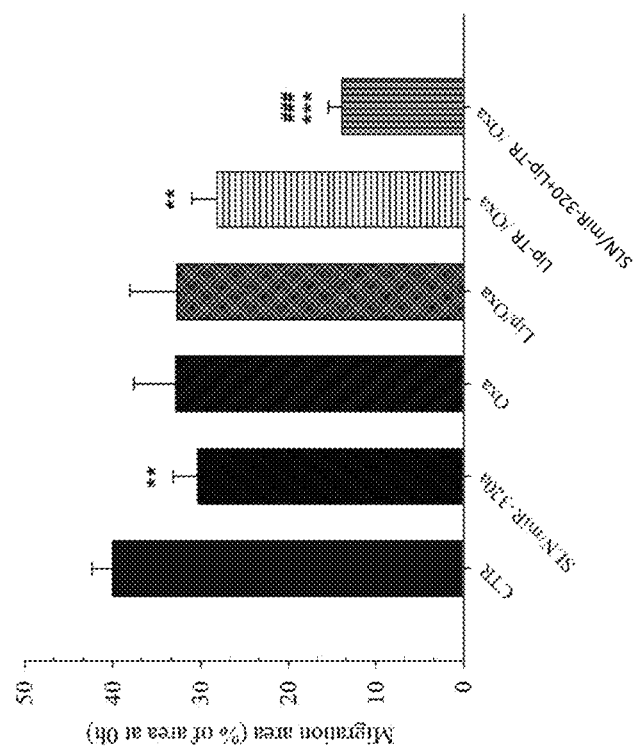
FIG. 6C shows the effect of different treatments of miR-320 and/or Oxa formulations on the relative migration percentage of HCT116 cells. Quantification of the relative percentage of cell migration area. P<0.01, *P<0.001 compared to CTR. ###P<0.001 compared to Lip-TR/Oxa.

Our results revealed that the combined treatment of SLN/miR-320 and Lip-TR/Oxa significantly inhibited cancer cell migration (FIG. 6D). Furthermore, the protein expression of epithelial marker E-cadherin was enhanced and the protein expressions of various regulation or metastasis factors, such as ZEB1, slug and snail, as well as the mesenchymal marker vimentin were considerably downregulated by the combined treatment of SLN/miR-320 and Lip-TR/Oxa (FIG. 6D). These results suggested that the combined treatment of SLN/miR-320 and Lip-TR/Oxa significantly suppressed migration and downregulated epithelial-mesenchymal transition (EMT)-associated protein expressions in cancer cells, thus inhibiting tumor metastasis and invasion.

Example 17. Measurement of Apoptosis

The Annexin V/PI double staining detection kit was used to detect the percentage of cells in viable, necrotic, or apoptotic status. Cells were seeded in 6-well plates. After overnight seeding of HCT116, HeLa and SAS cells, different formulations were added to the cells at 37° C. for 48 h and then stained with annexin V-propidium iodide (PI) labeling solution (Strong Biotech Corporation, Taiwan) in the dark. The collected cells were detected using a flow cytometer (BD Biosciences, San Jose, Calif., USA) equipped with an argon ion laser and operated at 488 nm. Data acquisition and analysis were performed using CELLQuest (BD Biosciences, San Jose, Calif., USA). Forward- and side-scatter signals were collected using linear scales, and fluorescence signals were collected on a logarithmic scale. Within each experiment, determinations were performed in triplicate.

Figure 7A:
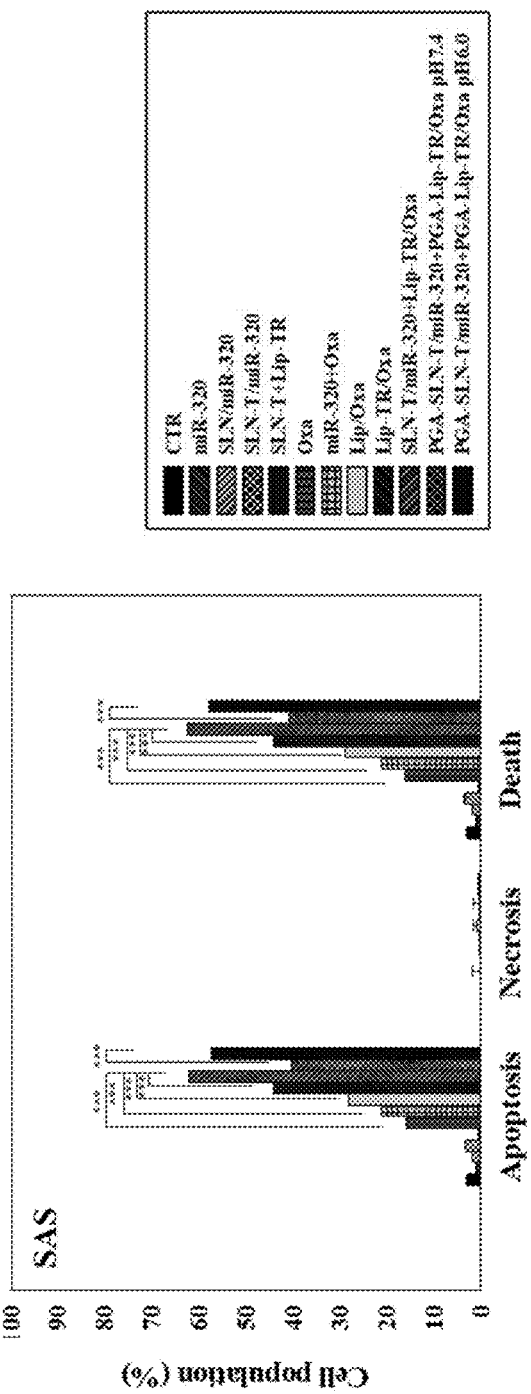
FIG. 7A-7C shows the effect of different treatments of miR-320 and/or Oxa formulations on apoptosis in different cancer cells. The Annexin V/PI kit was used to detect and quantify the percentage of apoptosis cells. The results are presented as mean SD. Differences at *P<0.05, P<0.01, and *P<0.001 were considered statistically significant. The combined treatment of SLN/miR-320 and Lip-TR/Oxa displayed higher apoptosis percentage than those of SLN/miR-320 or Lip-TR/Oxa alone in human cancer cells.
Figure 7B:
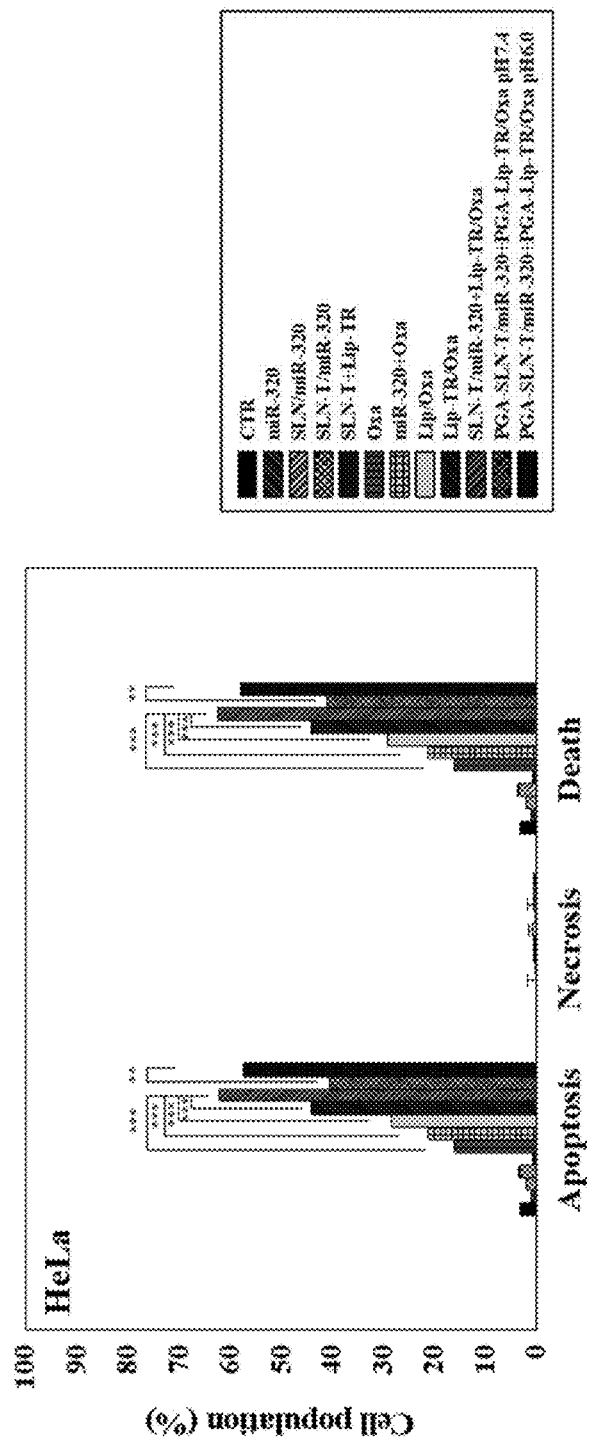
Figure 7C:
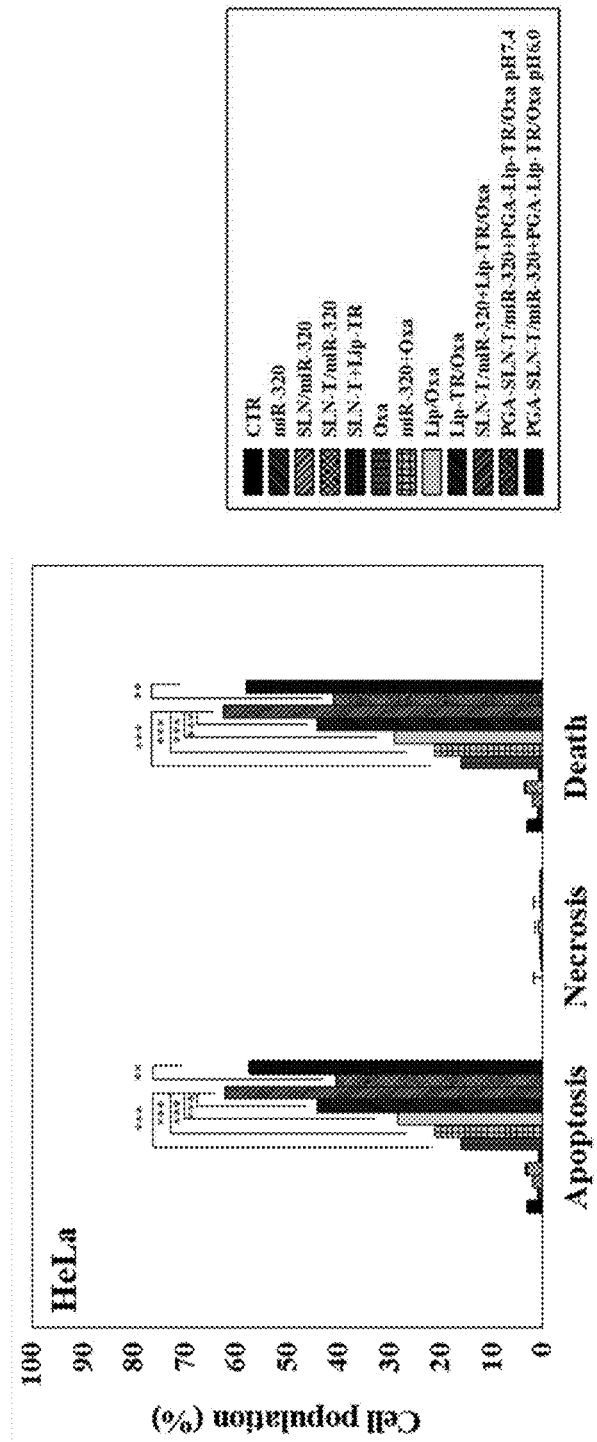
Figures 7D, 7E:
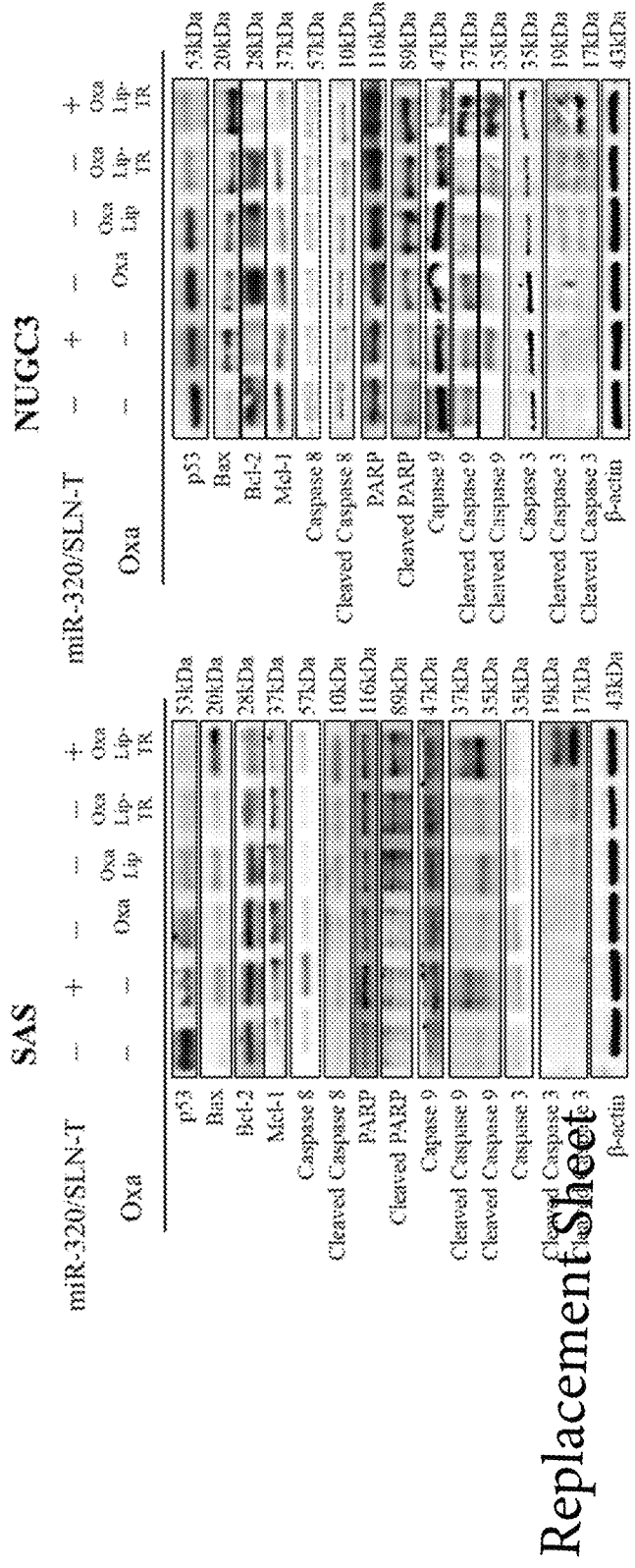
FIG. 7D-7F shows human cancer cells co-treated with SLN-T/miR-320 and Lip-TR/Oxa remarkably induced apoptosis through regulation of both extrinsic and intrinsic apoptosis pathways, as indicated by the apoptosis-associated protein expressions in different cancer cells by western blot assay.
Figure 7F:
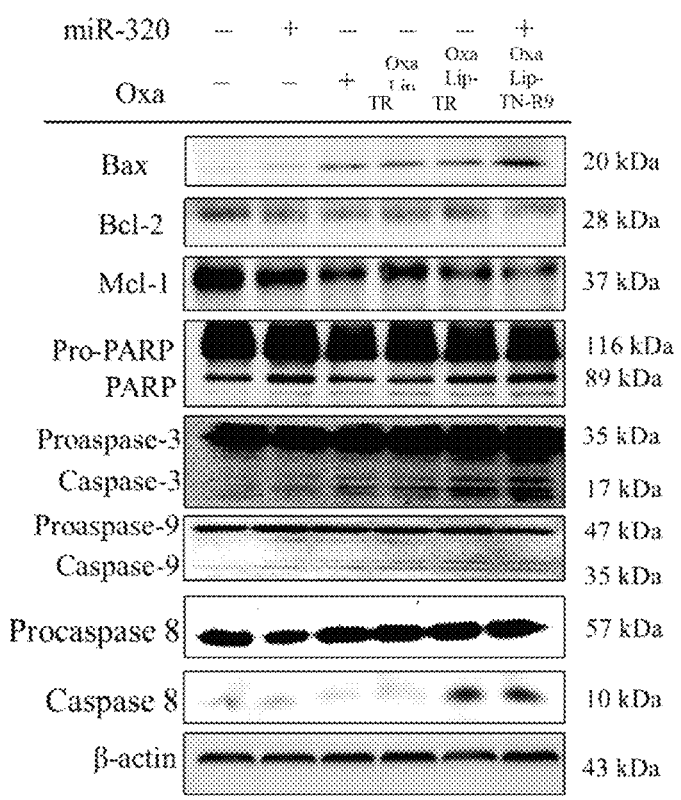

Effect of different treatments of miR-320 and/or Oxa formulations on apoptosis and the associated protein expressions in various cancer cells. The cells were pretreated with SLN-T/miR-320 and then treated with Oxa, Lip/Oxa or Lip-TR/Oxa. FIGS. 7A to 7C showed that apoptosis was induced to various degrees when HCT116, HeLa, SAS, and NUGC3 cells were treated with Oxa formulations with or without SLN-T/miR-320 using Annexin/PI and western blot assays. Furthermore, the combined treatment of SLN-T/miR-320 and Lip-TR/Oxa further enhanced apoptosis (FIG. 7A-7E). Concurrently, the protein expression levels of Bax, cleaved PARP, cleaved caspase-3, -8, and -9 were significantly upregulated and the protein expression levels of Bcl-2 and Mcl-1 were downregulated after the combined treatment of SLN/miR-320 and Lip-TR/Oxa (FIG. 7D-7E). Hence, human cancer cells co-treated with SLN/miR-320 and Lip-TR/Oxa significantly induced apoptosis through regulation of both extrinsic and intrinsic apoptosis pathways by Annexin V assay (FIG. 7A-7C) and western blotting study (FIG. 7D-7E).

Example 18. Establishment of In Vivo Mouse Tumor Model

BALB/c mice were purchased from National Laboratory Animal Center (Taipei, Taiwan) and maintained in the room at 22±1° C. with 55-60% relative humidity and 12-h light/dark cycle control. Enough sterilized food and water was supplied to these mice.

Example 19. In Vivo Bioluminescent Imaging

When BALB/c mice were at the age of 6-week with body weight of 20±2 g, they were injected with CT26/tk-luc cells expressing luciferase. After reaching the tumor size of 100 mm$^3$, mice were administered with PGA-SLN-T/miR-320 (1.25 mg/kg) and/or PGA-Lip-TR/Oxa (7 mg/kg) twice a week. Before taking images, CT26/tk-luc-bearing mice were i.p. injected with D-luciferin in PBS and sedated by isoflurane for 15 min. Tumor was examined by bioluminescence using the Xenogen IVIS50 Imaging system (Xenogen Corp., Alameda, Calif., USA). Images of bioluminescent signals were detected and recorded using Living Image software (Xenogen Corp.).

Figure 8A:
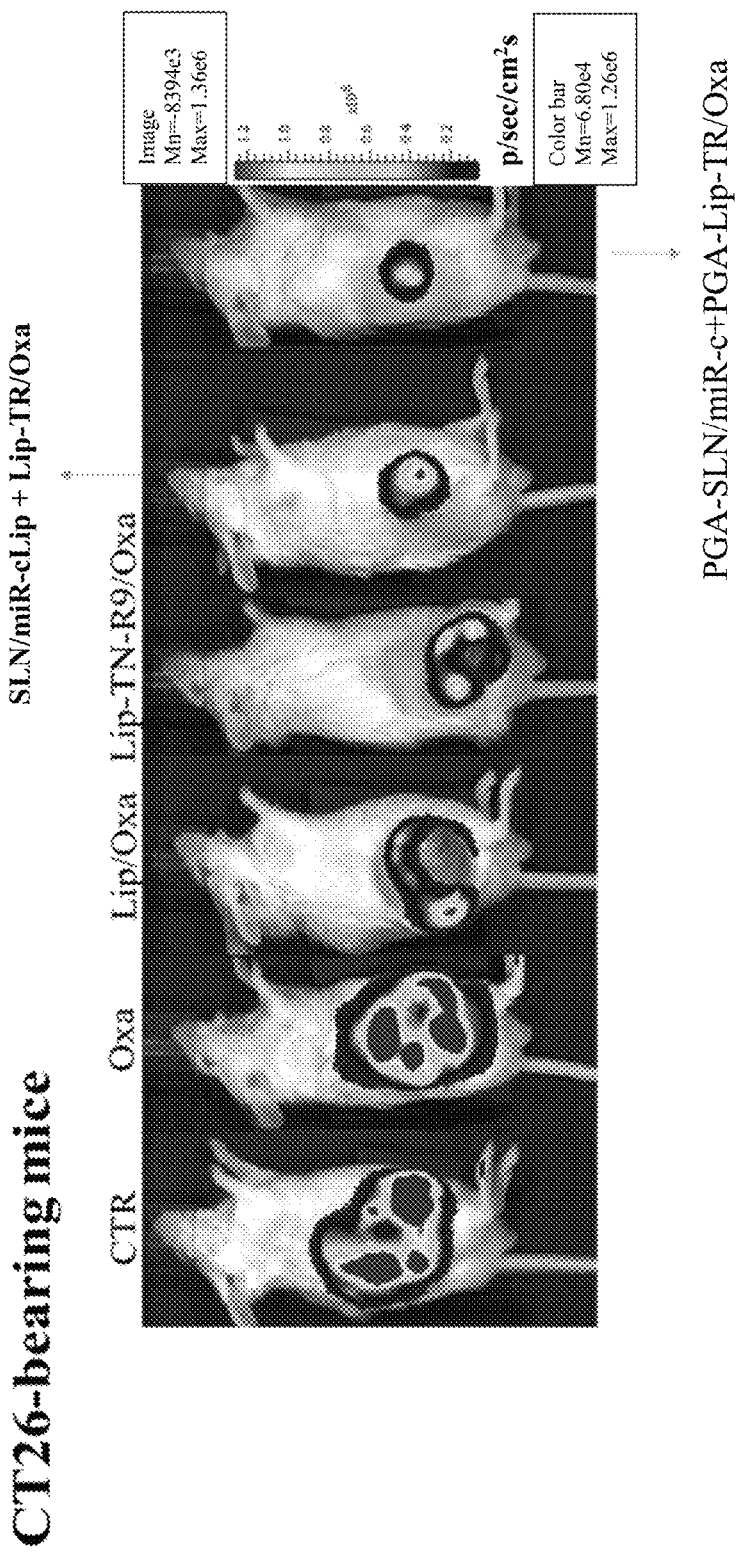
FIG. 8A-8B shows IVIS images of PGA-SLN-T/miR-320 and/or PGA-Lip-TR/Oxa in vivo. The BALB/c mice or nude (nu/nu) mice were injected with CT26 or SAS cells expressing luciferase. Mice were administered with PGA-SLN-T/miR-320 (1.25 mg/kg) and/or PGA-Lip-TR/Oxa (7 mg/kg) twice a week. On day 28 or day 14 after the beginning of intravenous injection of various formulations, the representative IVIS images of CT26- or SAS-bearing BALB/c mice were taken.
Figure 8B:
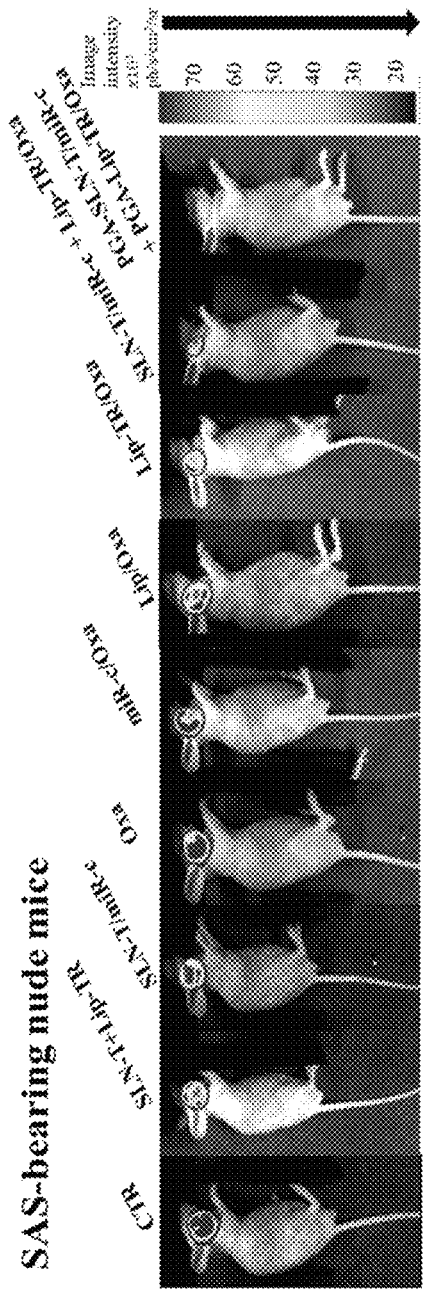

On day 28 or day 14 after the beginning of intravenous injection of various formulations, representative IVIS images of CT26- or SAS-bearing BALB/c mice were taken (FIG. 8A-8B).

In vivo IVIS images of oxaliplatin in different formulations were displayed as a function of time in CT26- or SAS-bearing BALB/c mice (FIG. 8A). Both CT26- or SAS-bearing mice without treatment (CTR) showed a high bioluminescence intensity in the tumor region as exposed by the IVIS images (FIG. 8A-8B). The bioluminescence intensity of the tumor-bearing mice treated with Oxa and/or miR-320 formulations was diminished to different extent, indicating the reduction in tumor size (FIG. 8A-8B). The combined treatment of tumor pH-shiftable PGA-SLN-T/miR-320 and PGA-Lip-TR/Oxa considerably decreased the bioluminescence intensity of tumors of both CRC and HNC to the lowest levels among all the treatment groups (FIG. 8A-8B).

Example 20. In Vivo Antitumor Efficacy

Figure 8C:
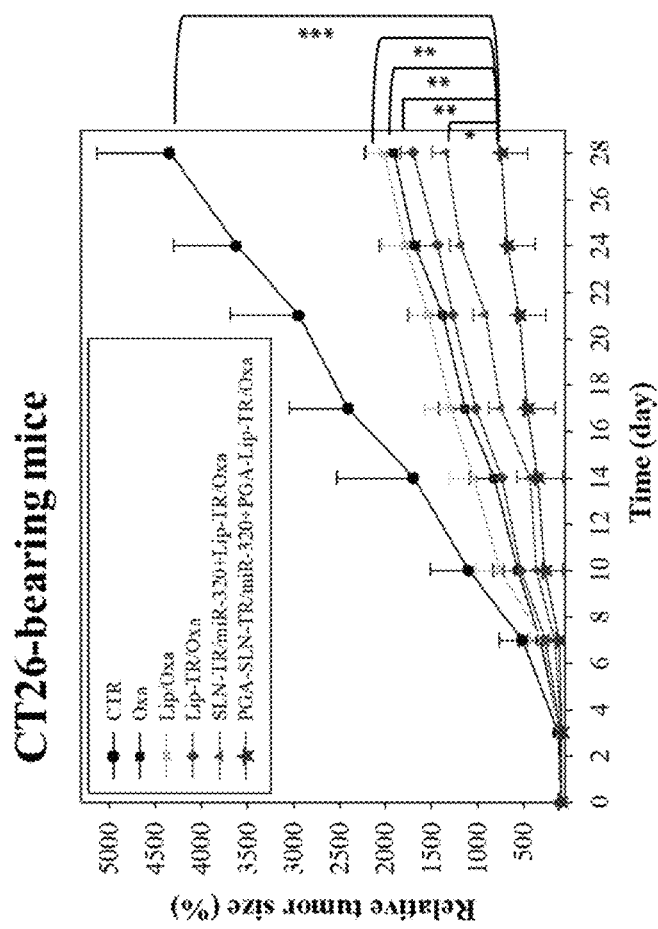
FIG. 8C-8D shows in vivo antitumor efficacy of oxaliplatin in different formulations as a function of time in CT26- or SAS-bearing BALB/c mice. The combined treatment of PGA-SLN-T/miR-320 and PGA-Lip-TR/Oxa reduced the tumor size of both CRC and HNC to the lowest levels among all the treatment groups. The data shown indicate the mean SD of four experiments. *Statistical significance at P<0.05; P<0.01; *P<0.001).
Figure 8D:
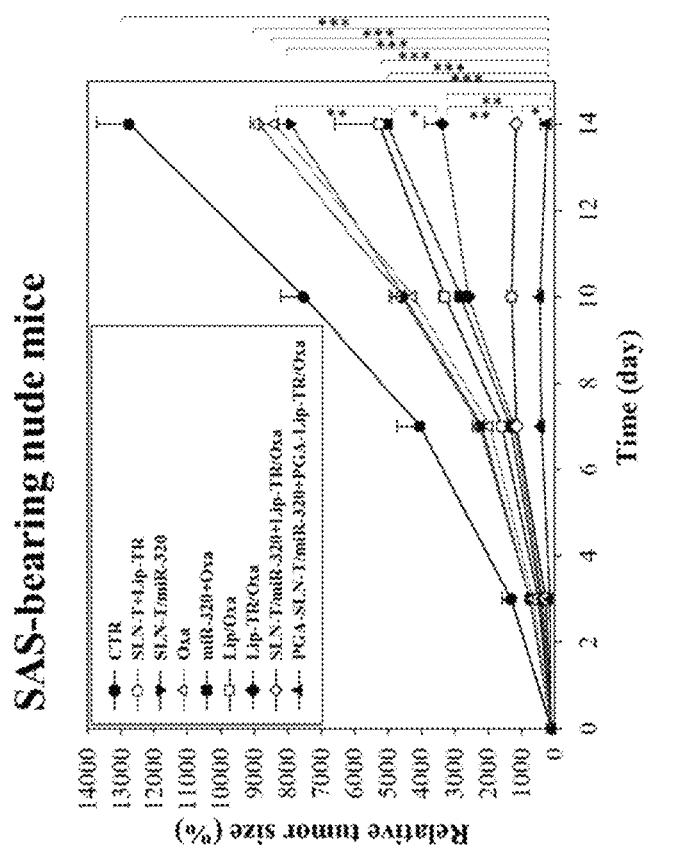

The BALB/c mice or nude (nu/nu) mice were injected with CT26 or SAS cells expressing luciferase. Mice were administered PGA-SLN-T/miR-320 (1.25 mg/kg) and/or PGA-Lip-TR/Oxa (7 mg/kg) twice a week. In vivo antitumor efficacy of oxaliplatin in different formulations was exhibited as a function of time in CT26- or SAS-bearing BALB/c mice (FIG. 8C-8D). The data shown indicate the mean SD of five experiments. *Statistical significance at $P<0.05$; $P<0.01$; *$P<0.001$. The combined treatment of PGA-SLN-T/miR-320 and PGA-Lip-TR/Oxa reduced the tumor size of both CRC and HNC to the lowest levels among all the treatment groups, illuminating the highest antitumor efficacy of this combined nanoparticle formulation among different treatment groups (FIG. 8C-8D).

Example 21. In Vivo Body Weight Measurement

Figure 8E:
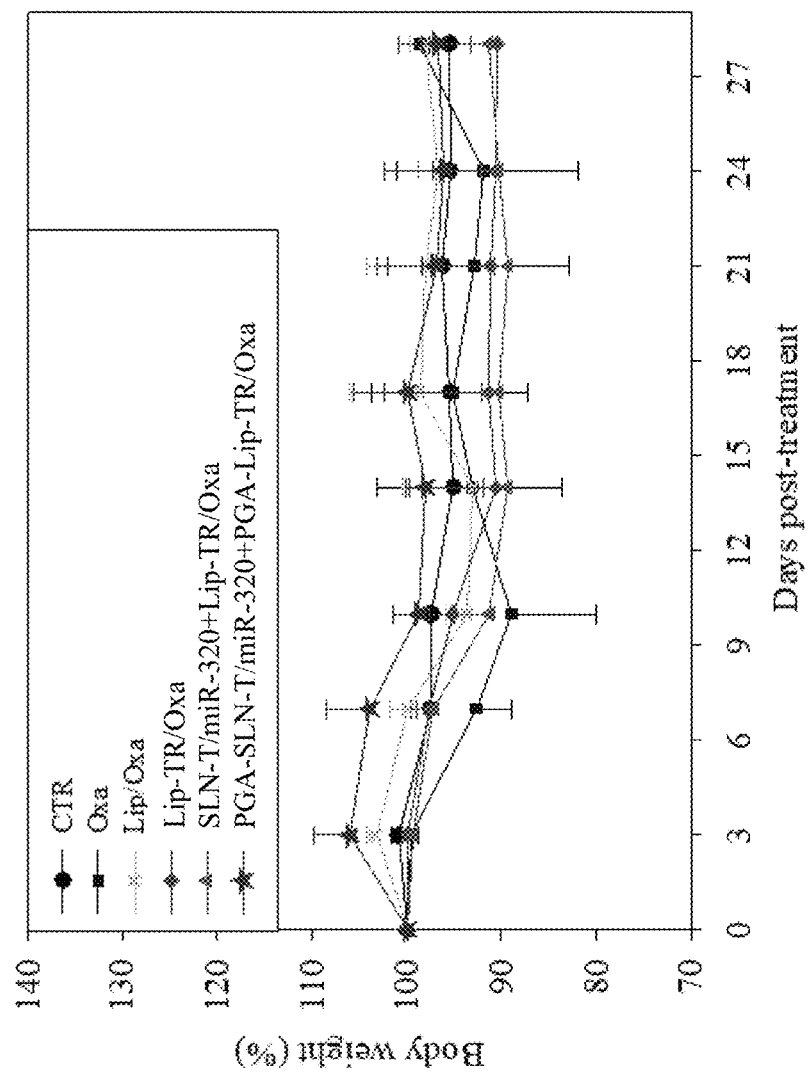
FIG. 8E shows the body weight (g) of CT26-bearing mice administered with different formulations of oxaliplatin and/or miR-320 as a function of time. There was no significant difference in the body weight among all the treatment groups in CRC mouse model.

The body weight (g) of CT26-bearing mice administered with different formulations of oxaliplatin was shown as a function of time (FIG. 8E). There was no significant difference in the body weight among all the treatment groups in both CRC (FIG. 8E) and HNC mouse model (data not shown).

Example 22. Biosafety Evaluation by Biochemical Tests and HE Staining

Tumor-bearing mice were treated as described above. Blood samples were taken from the orbital sinus of mice at 48 h after the final injection. The harvested samples were put at 37° C. to induce the clotting reaction and centrifuged for 15 min. The resultant serum samples were stored at −80° C. until further analysis. The functions of liver, kidney and heart were examined by detecting the serum levels of glutamate pyruvate transaminase (GPT), creatinine (CRE), and creatine kinase-MB (CK-MB) using the corresponding activity assay kits (Fujifilm, Tokyo, Japan) according to the manufacturer's instruction using a clinical dry chemistry analyzer (Fuji Dri-Chem 7000V, Fujifilm Corporation, Tokyo, Japan).

Additionally, tumor and various tissues were fixed in 4% paraformaldehyde overnight, embedded in paraffin, and cut into 5 m thick sections for hematoxylin and eosin (H&E) staining, and the histology was examined using Olympus microscope.

Biochemical tests after treatment with PGA-SLN-T/miR-320 and/or PGA-Lip-TR/Oxa in vivo. The Serum levels of glutamic oxaloacetic transaminase (GOT; liver function) or serum glutamate pyruvate transaminase (GPT; liver function), creatinine (CRE; renal function) and lactate dehydrogenase (LDH; heart function) or creatine kinase-MB (CK-MB; heart function) at 48 h after last treatment were shown in FIG. 9A-9B. Data shown indicate the mean±SD of four experiments.

Figures 9A, 9B, 9C:
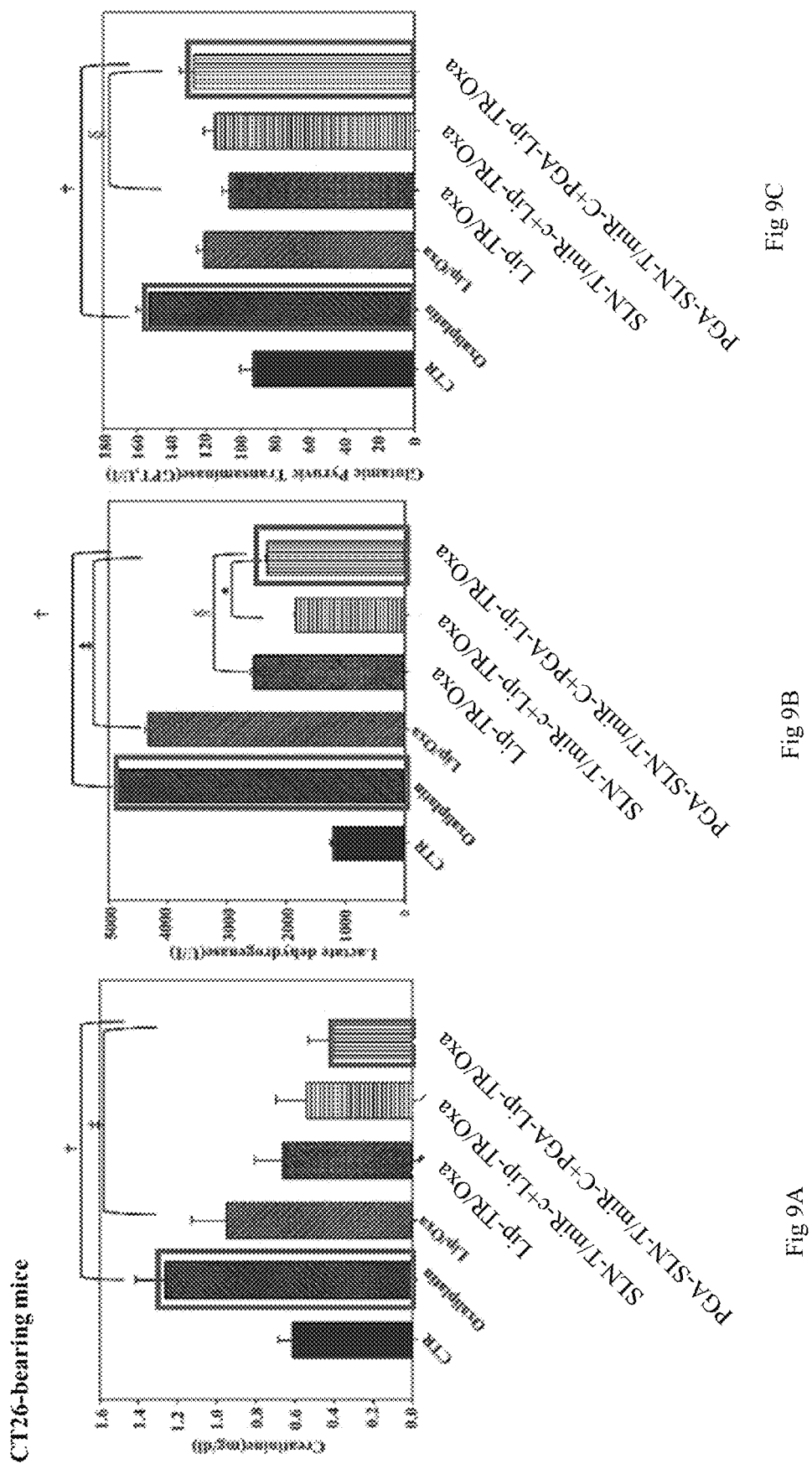
FIG. 9A-9F shows the biochemical tests after treatment with PGA-SLN-T/miR-320 and/or PGA-Lip-TR/Oxa in vivo for both CRC and HNC mouse models. Serum levels of glutamic oxaloacetic transaminase (GOT; liver function), creatinine (CRE; renal function) and lactate dehydrogenase (LDH; heart function) at 48 h after last treatment. Data shown indicate the mean SD of four experiments.
Figures 9D, 9E, 9F:
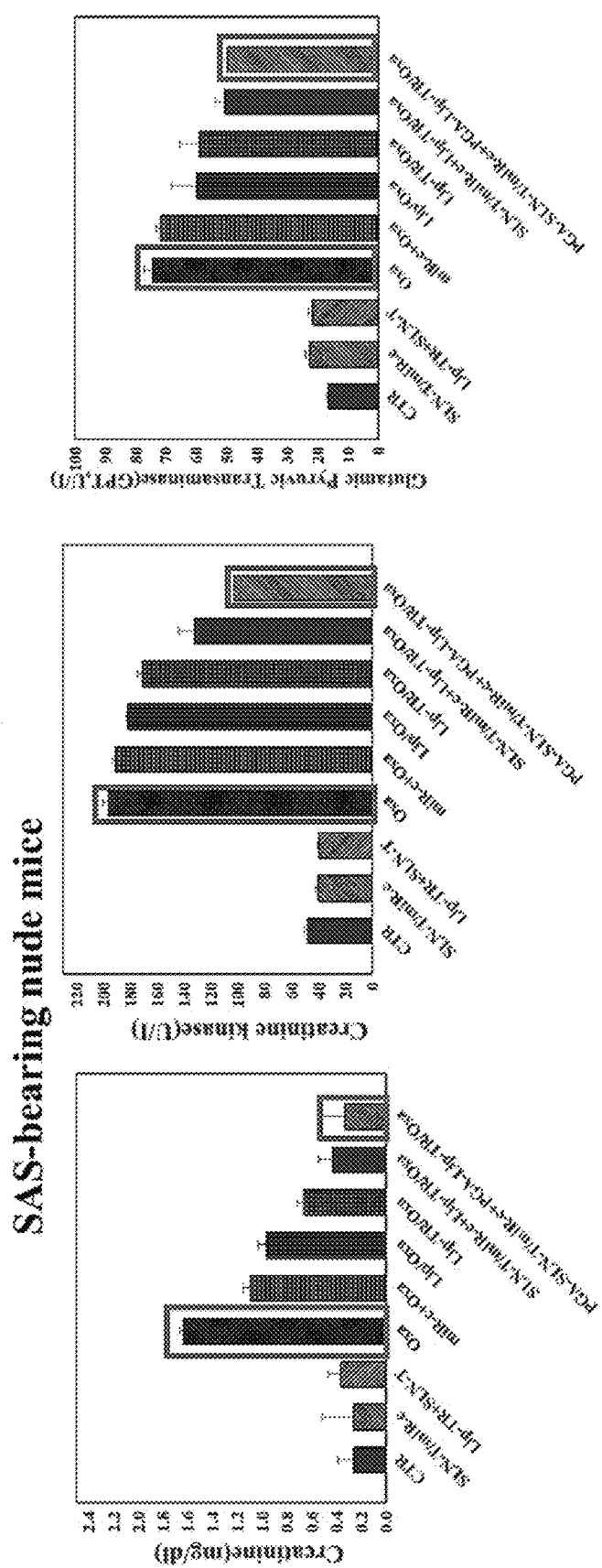

The results showed that serum CRE, CK-MB or LDH, and GPT or GOT levels were remarkably escalated after the treatments of Oxa or Oxa+ miR-320 (FIG. 9A-9B), demonstrsting the obvious damage of these Oxa and/or miR-320 formulations to the liver, kidney, and heart. Nonetheless, the serum levels of GPT or GOT, CRE, and CK-MB or LDH increased to less degees after the treatment of mice with Lip/Oxa or Lip-TR/Oxa compared with Oxa group. These three biochemical markers were reduced to great extents after the co-treatment of mice with SLN-T/miR-320 and Lip-TR/Oxa (FIG. 9A-9B). Particularly, the combined treatment of PGA-SLN-T/miR-320 and PGA-Lip-TR/Oxa decreased the values of these biochemical index to the lowest levels among all the treatment groups (FIG. 9A-9F).

Figure 9G:
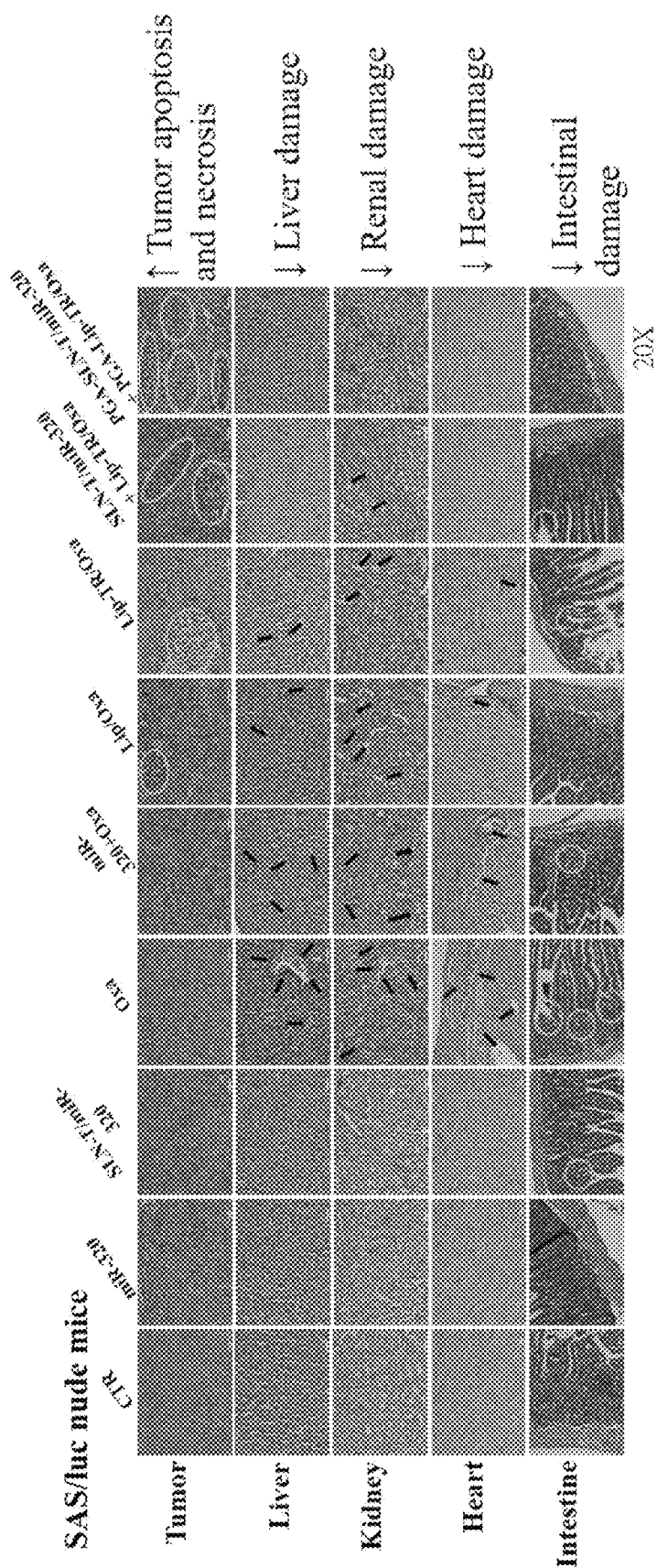
FIG. 9G show the H&E staining (×400) of tumor, kidney and liver tissues after injections of various formulations of oxaliplatin and/or miR-320 at the end of experiments in vivo for SAS-bearing mouse model. The combined treatment of PGA-SLN-T/miR-320 and PGA-Lip-TR/Oxa considerably reduced the toxicity of Oxa to heart, kidney and liver. The combined treatment of PGA-SLN-T/miR-320 and PGA-Lip-TR/Oxa remarkably increased the apoptosis and necrosis effect of tumor tissues in vivo for SAS-bearing mice; cycles in tumor: apoptosis and necrosis, arrows in liver, kidney or heart: inflammation, cycles in intestine: cell injury.
Figure 10:
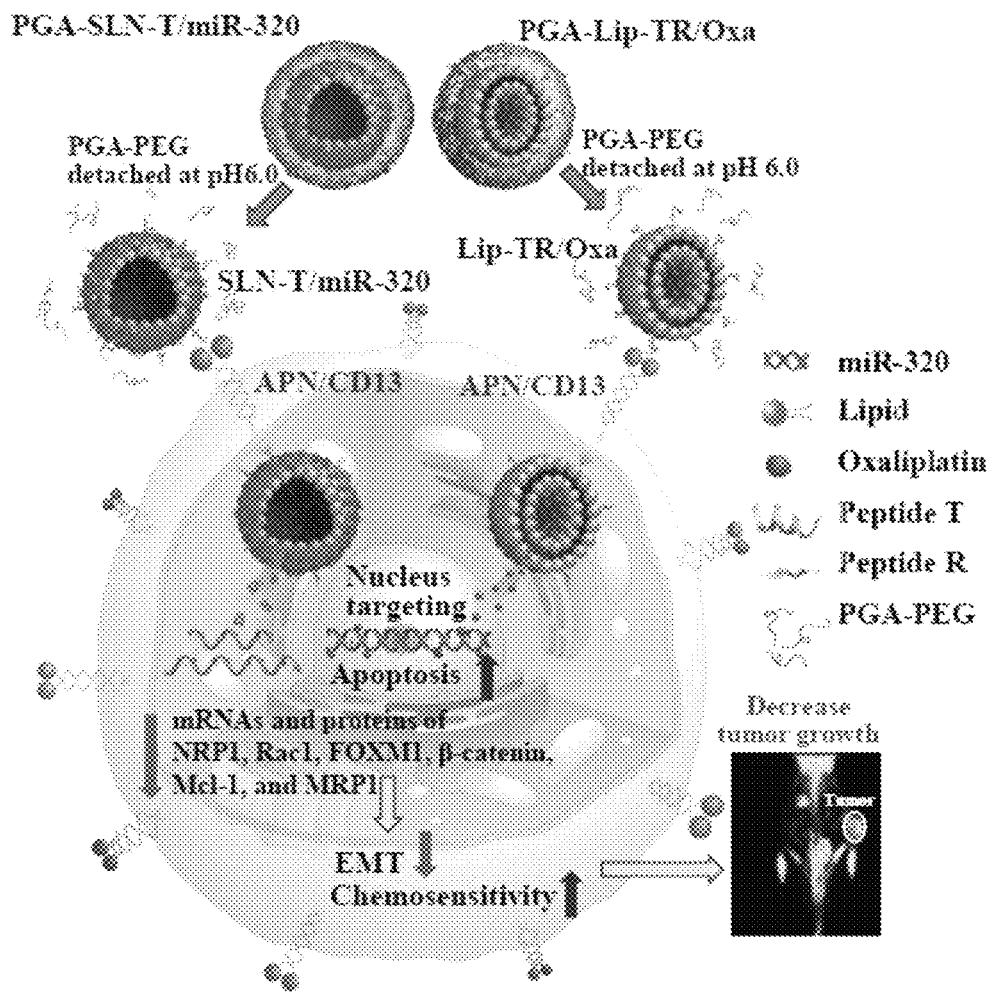
FIG. 10 shows the schematic summary of the pH-sensitive PGA-SLN-T/miR-320 and PGA-Lip-TR/Oxa responding to tumor extracellular pH to target the nucleus and cytoplasm for improvement in antitumor efficacy.
Figure 11:
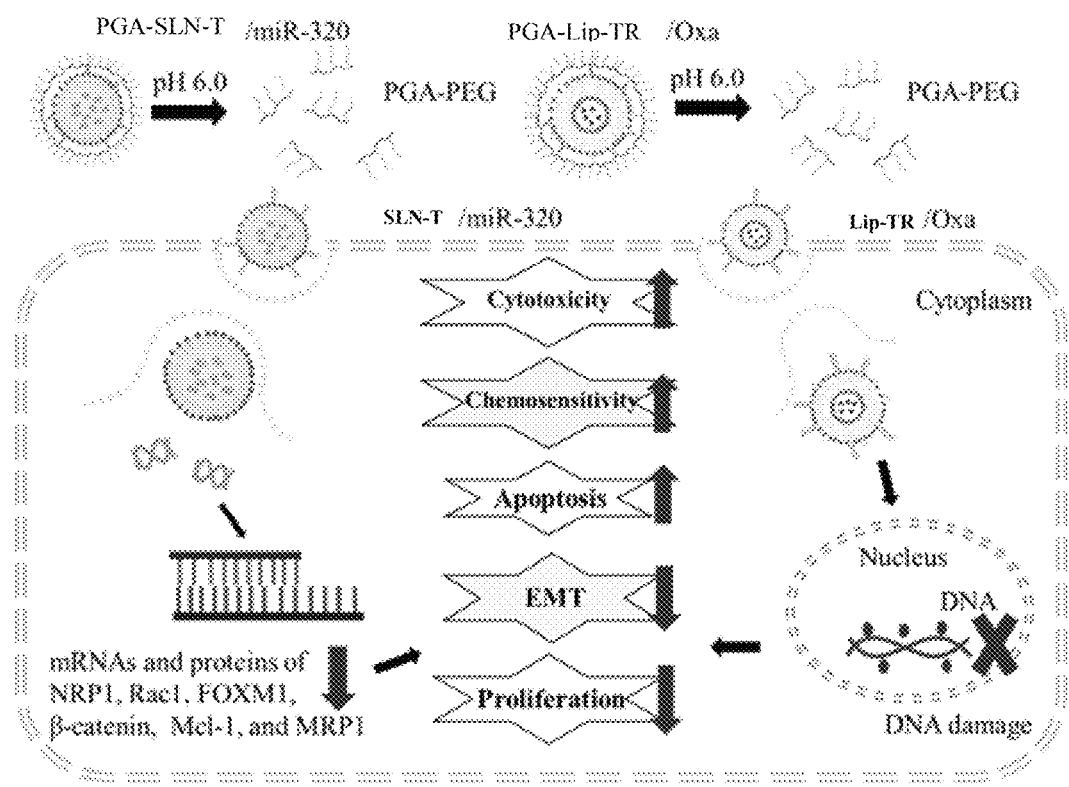
FIG. 11 demonstrates the pH-shiftable effect of the PGA-SLN-T/miR-320 and PGA-Lip-TR/Oxa at acidic tumor site for modulation of various signaling pathways to enhance chemosensitivity and apoptosis as well as to suppress metastasis and resistance in various cancer types.

The in vivo HE staining results of tumor tissues indicated that the tumor tissues of PGA-SLN-T/miR-320 and PGA-Lip-TR/Oxa group showed the most obvious phenomenon of nuclear chromatin condensation (pyknosis; circles of the first panel; FIG. 9G), denoting tumor apoptosis and necrosis (FIG. 9G; the first panel). The potential toxicity of these Oxa and/or miR-320 formulations on the liver, kidney, heart, and intestines was further examined through H&E staining (FIG. 9G, 2-5 panels). For comparison, the H&E staining of the intestines, kidney, heart, and liver of the control groups exhibited the integral cell morphology (FIG. 9G, 2-5 panels). The intestinal, renal, and liver tissues of all the treatment groups demonstrated interstitial hemorrhage (arrows), representing different degrees of tissue inflammation. The intestinal tissues also showed cell swelling, numerous vacuoles (potential indication of fatty degeneration; circles), and disordered cell arrangement, suggesting possible intestinal injury and inflammation (FIG. 9G, the 5th panel). Interestingly, our in vivo results also indicated that PGA-SLN-T/miR-320 and PGA-Lip-TR/Oxa produced only slight histopathological damage to the intestinal, renal, heart, or liver cells compared with other treatment groups (FIG. 9G, 2-5 panels). Moreover, the combined treatment of PGA-SLN-T/miR-320 and PGA-Lip-TR/Oxa verified a noteworthy decline in interstitial hemorrhage and tissue degeneration, which were the most severe in the Oxa group, denoting that tissue injury and inflammation were considerably alleviated by the co-treatment of PGA-SLN-T/miR-320 and PGA-Lip-TR/Oxa compared with those of Oxa group (FIG. 9G, 2-5 panels).

Example 23. Statistical Analysis

Statistical analysis was carried out using Student's t test and displayed as mean standard deviation (SD). Differences were defined to be significant at P<0.05.

CONCLUSIONS

Collectively, miR-320 may target diverse pathways, including NRP1, Rac, FOXM1, β-catenin, and Mcl-1 via inhibiting cell proliferation, cell cycle, MDR, and invasion, and thus re-sensitizes cancer cells to chemotherapy.

In this study, we have developed a novel combination therapy strategy based on the delivery of miR-320 and oxaliplatin by two different nanoparticles, named SLN-T and Lip-TR. At physiological pH, the negative charges of PEG-PGA in the outer shell may form a steric and charge barrier with positive charges of peptide T and R on the surface of Lip or SLN via electrostatic interaction to protect the peptide T and R from degradation by peptidases during the systemic circulation. In contrast, at acidic pH of tumor sites, the de-shielding of PEG-PGA layer may expose the cationic peptide T and R for enhancing targeting, cell penetration, and intracellular accumulation in the cancer cells. Both nanoparticles featured pH-responsiveness at the acidic environment and did not cause hemolysis and no cytotoxicity in normal rat small intestine cells or oral cells. SLN-T revealed better transfection efficiency compared to other commercial reagents. T and/or R peptides on the surface of liposomes and SLN facilitated the cellular uptake into various cancers. The combined treatment of SLN-T/miR-320 and Lip-TR/Oxa displayed higher cytotoxicity than SLN/miR-320 or Lip-TR/Oxa alone in human cancer cells. Human cancer cells treated with SLN/miR-320 and Lip-TR/Oxa significantly induced apoptosis through regulation of both extrinsic and intrinsic apoptosis pathways. Wnt/β-catenin pathway and its downstream MDR and EMT signaling pathway were also significantly inhibited by this combined treatment. These results suggested that the antitumor effect may attribute to not only induction of apoptosis, but also suppression of proliferation, drug efflux and EMT in cancer cells. This study demonstrated that the combined treatment of SLN-T/miR-320 and Lip-TR/Oxa could be used as a novel and potential anticancer strategy.

The invention claimed is:

1. pH-shiftable nanoparticles, comprising:
solid lipid nanoparticles (SLN) and liposomes (LIP),
a surface of a nanoparticle core of the SLN and of the LIP, wherein the surface of the nanoparticle core of the SLN and the LIP is modified with a cationic target molecule,
a therapeutic agent inside the nanoparticle core of the SLN and the LIP; and
an outer layer surrounding the outside surface of the nanoparticle core of the SLN and of the LIP, the outer layer is coated with an acid-detachable polymer, wherein the acid-detachable polymer is pH sensitive and responds to acidic pH;
wherein the cationic target molecule on the surface of the nanoparticle core of the SLN and of the LIP and the acid-detachable polymer on the outer layer form a space and charge barrier via electrostatic interaction,
wherein the cationic target molecule of the SLN is a bifunctional peptide, wherein the bifunctional peptide possesses features of a tumor-homing moiety and cell-penetrating properties, wherein the bifunctional peptide is T peptide SEQ ID NO: 3,
wherein the cationic target molecules of the LIP are the bifunctional peptide and a cell nucleus-targeted peptide, wherein the bifunctional peptide is T peptide SEQ ID NO: 3, and wherein the cell nucleus-targeted peptide is R peptide SEQ ID NO: 4.

2. The pH-shiftable nanoparticles of claim 1, wherein the acid-detachable polymer is a PGA-PEG.

3. The pH-shiftable nanoparticles of claim 1, wherein the nanoparticle core of the SLN and of the LIP is L-α-phosphatidylcholine, glycerol monostearate, glycerol monopalmitate, glycerol monooleate, DSPE, DPPE, DOPE, DOTAP, DOTMA, SAINT 2, MC3 or KC2.

4. The pH-shiftable nanoparticles of claim 1, wherein the therapeutic agent of the SLN is a microRNA, wherein the therapeutic agent of the LIP is an anticancer drug.

5. The pH-shiftable nanoparticles of claim 4, wherein the microRNA is a hsa-miR-21 inhibitor or a microRNA mimic, wherein the microRNA mimic is selected from the group consisting of has-miR-122-5p, hsa-miR-125b-5p, has-miR-136-5p, has-miR-139-5p, hsa-miR-142-5p, has-miR-200c-3p and has-miR-320a.

6. The pH-shiftable nanoparticles of claim 4, wherein the anticancer drug is selected from the group consisting of irinotecan, oxaliplatin, epirubicin, doxorubicin, afatinib and docetaxel.

7. The pH-shiftable nanoparticles of claim 1, wherein the pH-sensitive polymer on the outer layer of the pH-shiftable nanoparticles becomes protonated and detached from the SLN and the LIP in a pH 5-6.5 environment or tumor microenvironment.

8. The pH-shiftable nanoparticles of claim 1, wherein the SLN nanoparticles are constructed by a conjugate of DSPE-PEG-T and the bifunctional peptide.

9. The pH-shiftable nanoparticles of claim 1, wherein the LIP are constructed by a conjugate of DSPE-PEG-R and the cell nucleus-targeted peptide, and a conjugate of DSPE-PEG-T and the bifunctional peptide.

10. The pH-shiftable nanoparticles of claim 1, wherein the nanoparticle size is smaller than 150 nm with narrow size distribution.

11. A pharmaceutical composition comprising:
a therapeutically effective amount of pH-shiftable nanoparticles as claimed in claim 1.

12. The pharmaceutical composition of claim 11, comprising:
a microRNA-loaded SLN comprising a mixture of a monoglyceride, a cationic lipid and a surfactant; and a drug-loaded LIP comprising an anticancer drug and a lipid bilayer composed of a phospholipid.

13. The pharmaceutical composition of claim 12, wherein the microRNA is a hsa-miR-21 inhibitor or a microRNA mimic, wherein the microRNA mimic is selected from the group consisting of has-miR-122-5p, hsa-miR-125b-5Sp, has-miR-136-5p, has-miR-139-5p, hsa-miR-142-5p, has-miR-200c-3p and has-miR-320.

14. The pharmaceutical composition of claim 12, wherein the SLN is PGA-SLN-T and the microRNA is miR-320.

15. The pharmaceutical composition of claim 12, wherein the anticancer drug is selected from the group consisting of irinotecan, oxaliplatin, epirubicin, doxorubicin, afatinib and docetaxel.

16. The pharmaceutical composition of claim 12, wherein the LIP is PGA-LIP-TR and the anticancer drug is oxaliplatin.

17. The pharmaceutical composition of claim 11, wherein the pH-shiftable nanoparticles are modified with peptide T and peptide R.

18. A method for treating cancer in a subject, comprising:
administering a therapeutically effective amount of pH-shiftable nanoparticles as claimed in claim 1, comprising:
a microRNA-loaded SLN comprising a mixture of a monoglyceride, a cationic lipid, and a surfactant; and
a LIP comprising an anticancer drug and a lipid bilayer composed of a phospholipid.

19. The method of claim 18, wherein the cancer comprises colorectal cancer, head and neck cancer, gastric cancer or cervical cancer.

20. The method of claim 18, wherein the anticancer drug is selected from the group consisting of irinotecan, oxaliplatin, epirubicin, doxorubicin, afatinib and docetaxel.

21. The method of claim 18, wherein the microRNA is a hsa-miR-21 inhibitor or a microRNA mimic, wherein the microRNA mimic is selected from the group consisting of has-miR-122-5p, hsa-miR-125b-5p, has-miR-136-5p, has-miR-139-5p, hsa-miR-142-5p, has-miR-200c-3p and has-miR-320.

22. The method of claim 18, wherein the pH-shiftable nanoparticles are coated with PGA-PEG on the outer layer.

23. The method of claim 18, wherein the pH-shiftable nanoparticles are de-coated of pH-sensitive polymers on the outer layer at pH 6.0 to expose peptide T and peptide R.

* * * * *

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial Sequence
<220> FEATURE:
<223> OTHER INFORMATION: cell-penetrating peptide

<400> SEQUENCE: 1

Cys Ala Tyr Gly Arg Lys Lys Arg Arg Gln Arg Arg Arg
1               5                   10

<210> SEQ ID NO 2
<211> LENGTH: 8
<212> TYPE: PRT
<213> ORGANISM: Artificial Sequence
<220> FEATURE:
<223> OTHER INFORMATION: tumor-homing peptide
```

```
<400> SEQUENCE: 2

Arg Asn Gly Arg Gly Pro Asp Cys
1               5

<210> SEQ ID NO 3
<211> LENGTH: 21
<212> TYPE: PRT
<213> ORGANISM: Artificial Sequence
<220> FEATURE:
<223> OTHER INFORMATION: bifunctional peptide possesses features of
      tumor-homing moiety and cell-penetrating property

<400> SEQUENCE: 3

Ala Tyr Gly Arg Lys Lys Arg Arg Gln Arg Arg Arg Cys Arg Asn Gly
1               5                   10                  15

Arg Gly Pro Asp Cys
            20

<210> SEQ ID NO 4
<211> LENGTH: 9
<212> TYPE: PRT
<213> ORGANISM: Artificial Sequence
<220> FEATURE:
<223> OTHER INFORMATION: nucleus-targeted peptide

<400> SEQUENCE: 4

Cys Arg Arg Lys Arg Arg Arg Arg Arg
1               5
```